(12) United States Patent
Fukushi et al.

(10) Patent No.: US 11,375,924 B2
(45) Date of Patent: Jul. 5, 2022

(54) WALKING STATE MEASUREMENT DEVICE, WALKING STATE MEASUREMENT SYSTEM, WALKING STATE MEASUREMENT METHOD, AND STORAGE MEDIUM FOR STORING WALKING STATE MEASUREMENT PROGRAM

(71) Applicant: NEC Corporation, Tokyo (JP)

(72) Inventors: Kenichiro Fukushi, Tokyo (JP); Takeo Nozaki, Tokyo (JP)

(73) Assignee: NEC CORPORATION, Tokyo (JP)

( * ) Notice: Subject to any disclaimer, the term of this patent is extended or adjusted under 35 U.S.C. 154(b) by 475 days.

(21) Appl. No.: 16/462,617

(22) PCT Filed: Nov. 17, 2017

(86) PCT No.: PCT/JP2017/041408
§ 371 (c)(1),
(2) Date: May 21, 2019

(87) PCT Pub. No.: WO2018/101071
PCT Pub. Date: Jun. 7, 2018

(65) Prior Publication Data
US 2020/0054249 A1    Feb. 20, 2020

(30) Foreign Application Priority Data
Nov. 29, 2016  (JP) .............................. JP2016-231395

(51) Int. Cl.
*A61B 5/11* (2006.01)
*A61B 5/00* (2006.01)
*A61B 5/103* (2006.01)

(52) U.S. Cl.
CPC ............ *A61B 5/112* (2013.01); *A61B 5/1036* (2013.01); *A61B 5/1123* (2013.01);
(Continued)

(58) Field of Classification Search
CPC ..... A61B 5/112; A61B 5/1123; A61B 5/1107; A61B 5/6807; A61B 5/6829; A61B 5/1036; A61B 5/1038
See application file for complete search history.

(56) References Cited

U.S. PATENT DOCUMENTS

2006/0197485 A1* 9/2006 Kawai .................. B62D 57/032
                                                          318/568.12
2014/0343460 A1* 11/2014 Evans, III ............ A61B 5/6829
                                                          600/595

FOREIGN PATENT DOCUMENTS

JP      2007236663 A    9/2007
JP      4390129 B2     12/2009
(Continued)

OTHER PUBLICATIONS

A. Forner Cordero et al., "Use of pressure insoles to calculate the complete ground reaction forces", Journal of Biomechanics, vol. 37, pp. 1427-1432, 2004 (12 pages total).

(Continued)

*Primary Examiner* — Paul M. West

(57) ABSTRACT

A walking state measurement device according to the present invention includes: at least one memory storing a set of instructions; and at least one processor configured to execute the set of instructions to: estimate a floor reaction force by use of at least either of motion data and lower limb vertical load data of a walker, and outputting the floor reaction force as floor reaction force data; and calculate a walking state of the walker by use of at least either of the motion data and the floor reaction force data, and outputting the walking state.

19 Claims, 12 Drawing Sheets

(52) U.S. Cl.
CPC .......... *A61B 5/6807* (2013.01); *A61B 5/6828* (2013.01); *A61B 5/6829* (2013.01); *A61B 2562/0219* (2013.01); *A61B 2562/0247* (2013.01)

(56) References Cited

FOREIGN PATENT DOCUMENTS

| | | | |
|---|---|---|---|
| JP | 2010273748 | A | 12/2010 |
| JP | 4860430 | B2 | 1/2012 |
| JP | 2012161402 | A | 8/2012 |
| JP | 2014027978 | A | 2/2014 |
| JP | 2015202141 | A | 11/2015 |
| JP | 2016041155 | A | 3/2016 |
| JP | 2016150193 | A | 8/2016 |
| WO | 2015164706 | A1 | 10/2015 |

OTHER PUBLICATIONS

International Search Report dated Feb. 6, 2018, in counterpart International Application No. PCT/JP2017/041408.
Written opinion of the International Searching Authority dated Feb. 6, 2018, in counterpart International Application No. PCT/ JP2017/ 041408.

* cited by examiner

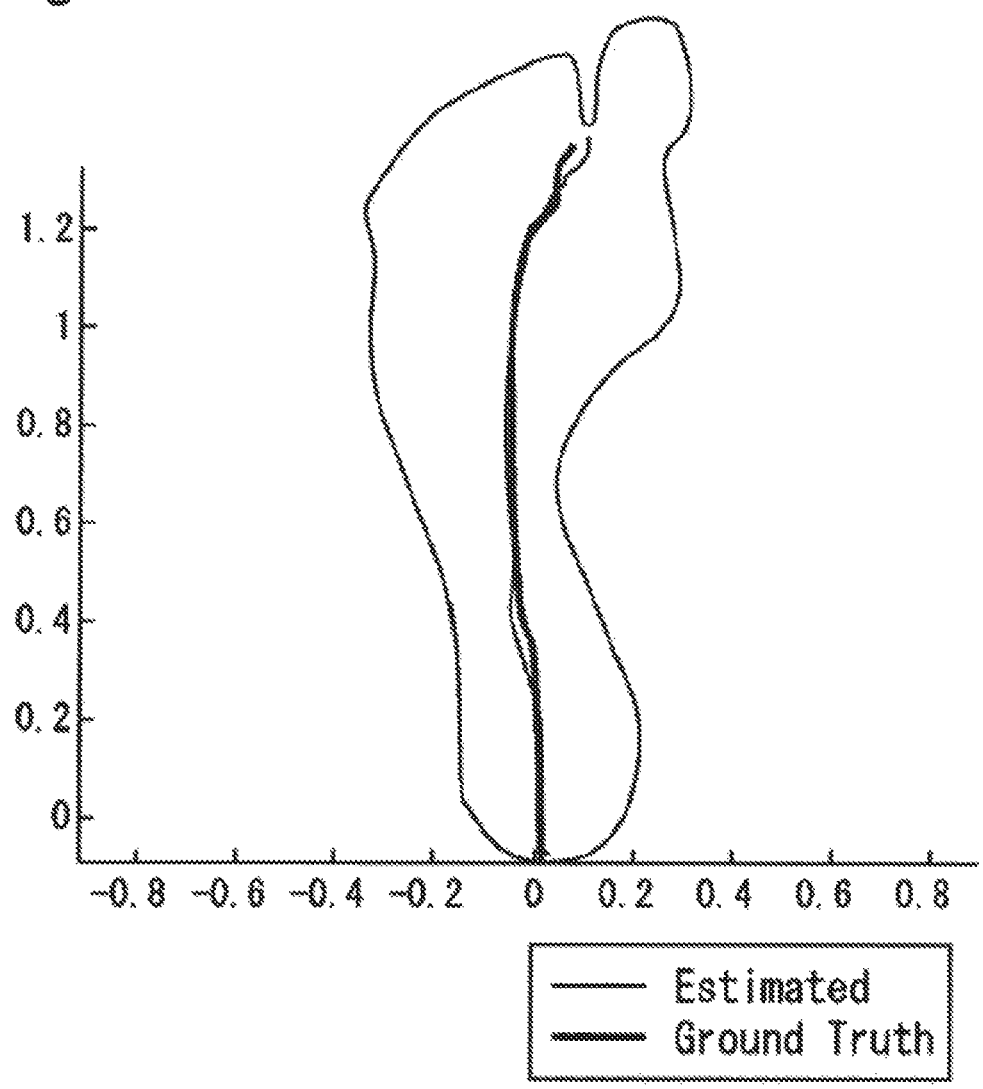

WALKING STATE MEASUREMENT DEVICE, WALKING STATE MEASUREMENT SYSTEM, WALKING STATE MEASUREMENT METHOD, AND STORAGE MEDIUM FOR STORING WALKING STATE MEASUREMENT PROGRAM

This application is a National Stage Entry of PCT/JP2017/041408 filed on Nov. 17, 2017, which claims priority from Japanese Patent Application 2016-231395 filed on Nov. 29, 2016, the contents of all of which are incorporated herein by reference, in their entirety.

TECHNICAL FIELD

The present invention relates to a walking state measurement device, a walking state measurement system, a walking state measurement method, and a storage medium for storing a walking state measurement program, and particularly relates to a walking state measurement device, a walking state measurement system, a walking state measurement method, and a storage medium for storing a walking state measurement program that enable easy measurement of a walking state of a walker.

BACKGROUND ART

In order to support targets such as an aged person and a patient undergoing rehabilitation, a technology allowing easy measurement of a walking state of the target in daily life has been sought.

When measuring a walking state in the present situation of technologies, a technology of measuring, by use of a measurement device composed of a motion capture device and a force plate, a motion of a walker by the motion capture device, and three component forces of a floor reaction force (a vertical component force, a lateral component force, and a longitudinal component force) and a point of application of the floor reaction force (coordinate values on the floor surface) by the force plate, and then measuring a walking state, based on inverse dynamic calculation, is commonly used. Joint torque at a hip joint, a knee joint, an ankle joint, and the like, muscle tension and amounts of muscle activity at a hamstring, quadriceps, and the like, and in addition, a metabolic cost may be measured as the walking state.

However, the force plate needs to be installed on the floor surface in the aforementioned technology, and therefore it is difficult to easily measure a walking state of a target in daily life. Then, a technology of measuring a walking state of a walker by use of, for example, a sensor reacting to a floor reaction force, such as a pressure sensor, being arranged on a surface of a shoe which a walker wears and walks with, in place of the force plate is proposed.

"ESTIMATION SYSTEM OF LOWER LIMB JOINT MOMENT AND LOWER LIMB MUSCLE TENSION USING SOLE PRESSURE" as PTL 1 being Japanese Patent No. 4390129 describes a technology of estimating a floor reaction force, a lower limb joint moment, and lower limb muscle tension by use of a measurement value of a sensor reacting to a floor reaction force, such as a pressure sensor, being arranged on a surface of a shoe which a subject wears and walks with.

"LOAD MEASUREMENT DEVICE" as PTL 2 being Japanese Patent No. 4860430 describes a technology related to a sheet-shaped load measurement device independent of a load distribution. The technology in PTL 2 allows measurement of a total amount of vertical load applied to a sole surface, that is, a vertical component force of a floor reaction force, independently of a size and a shape of a foot of a user.

PTL 3 discloses a technology of evaluating a motion characteristic of a subject, based on pressure placed on left and right sole regions of the subject and positional transition of the sole regions.

PTL 4 describes a technology of calculating a moving distance of a human, a moving speed of the human, and a floor reaction force, based on signals from a plurality of attitude sensors, such as acceleration sensors, attached to the human body.

"Use of pressure insoles to calculate the complete ground reaction forces" by A. Forner Cordero, et al. as NPL 1 describes a technology of estimating a floor reaction force and a lower limb joint moment by use of a measurement value of a pressure sensor array arranged on a sole surface.

CITATION LIST

Patent Literature

PTL 1: Japanese Patent No. 4390129
PTL 2: Japanese Patent No. 4860430
PTL 3: Japanese Unexamined Patent Application Publication No. 2012-161402
PTL 4: Japanese Unexamined Patent Application Publication No. 2016-150193

Non Patent Literature

NPL 1: A. Forner Cordero et al., "Use of pressure insoles to calculate the complete ground reaction forces," Journal of Biomechanics, Vol. 37, No. 9, pp. 1427 to 1432, 2004

SUMMARY OF INVENTION

Technical Problem

However, the technology described in each of PTL 1, PTL 2, PTL 3, and NPL 1 that are related to the present invention has a problem described below.

First, the technology in PTL 1 requires sensors reacting to a floor reaction force, such as pressure sensors, being arranged in at least four spots or more on a shoe surface. Then, while the sensors need to be arranged in suitable positions (a heel region, an arch region, a metatarsal region, and a toe region), such suitable positions vary by a size and a shape of a foot of a target; and therefore there is a problem that adjustment for each target is required and it takes time to make the adjustment. The technology described in PTL 3 also has a similar problem.

On the other hand, as described above, the technology in PTL 2 allows measurement of a total amount of vertical load applied to a sole surface, that is, a vertical component force of a floor reaction force, independently of a size and a shape of a foot of a target, and therefore does not require adjustment of an arrangement position of a sensor. However, component forces of a floor reaction force other than a vertical component force and a point of application cannot be measured. In other words, a lateral component force and a longitudinal component force of a floor reaction force, and a point of application of the floor reaction force cannot be measured. Accordingly, it is difficult to measure a walking state, based on inverse dynamic calculation as described above.

The technology in NPL 1 uses a measurement device including an array of 86 to 99 pressure sensors. Since such a large number of pressure sensors measure a load on an entire sole surface, adjustment of positions of the sensors for each target is not required; however, there is a problem that the measurement device becomes expensive and an economic burden on a user increases.

As described above, it is difficult to easily measure a walking state of a target in daily life in the present situation of the technologies related to the present invention.

Object of Present Invention

The present invention has been made in view of such problems, and an object of the present invention is to provide a walking state measurement device, a walking state measurement system, a walking state measurement method, and a walking state measurement program that enable easy measurement of a walking state of a walker, regardless of a shape and a size of a foot of the walker.

Solution to Problem

In order to resolve the aforementioned problems, a walking state measurement device, a walking state measurement system, a walking state measurement method, and a walking state measurement program, according to the present invention, mainly employ characteristic configurations as follows.

A walking state measurement device according to an aspect of the present invention includes:

a floor reaction force estimation means for estimating a floor reaction force by use of at least either of motion data and lower limb vertical load data of a walker, and outputting the floor reaction force as floor reaction force data; and a walking state calculation means for calculating a walking state of the walker by use of at least either of the motion data and the floor reaction force data, and outputting the walking state.

A walking state measurement system according to an aspect of the present invention includes:

a motion measurement means for acquiring motion data of a walker;

a lower limb vertical load measurement means for acquiring lower limb vertical load data of the walker; and a walking state measurement means for calculating a walking state of the walker by use of at least either of the motion data acquired in the motion measurement means and the lower limb vertical load data acquired in the lower limb vertical load measurement means, and outputting the walking state.

A walking state measurement method according to an aspect of the present invention includes:

estimating a floor reaction force by use of at least either of motion data and lower limb vertical load data of a walker, and outputting the floor reaction force as floor reaction force data; and calculating a walking state of the walker by use of at least either of the motion data and the floor reaction force data, and outputting the walking state.

A storage medium according to an aspect of the present invention stores a walking state measurement program causing a computer to execute walking state measurement processing including:

floor reaction force estimation processing of estimating a floor reaction force by use of at least either of motion data and lower limb vertical load data of a walker, and outputting the floor reaction force as floor reaction force data; and walking state calculation processing of calculating a walking state of the walker by use of at least either of the motion data and the floor reaction force data, and outputting the walking state. The aspect of the present invention may also be provided by the walking state measurement program stored in the aforementioned storage medium.

Advantageous Effects of Invention

A walking state measurement device, a walking state measurement system, a walking state measurement method, and a storage medium for storing a walking state measurement program, according to the present invention, provide an effect that an arrangement position of a sensor reacting to a floor reaction force, such as a pressure sensor, being arranged on a surface of a shoe which a walker wears and walks with does not need to be adjusted for each target.

BRIEF DESCRIPTION OF DRAWINGS

FIG. 8B is a graph illustrating an example of an output result of the floor reaction force estimation unit in the example 1 of the present invention.

EXAMPLE EMBODIMENT

Figure 1:
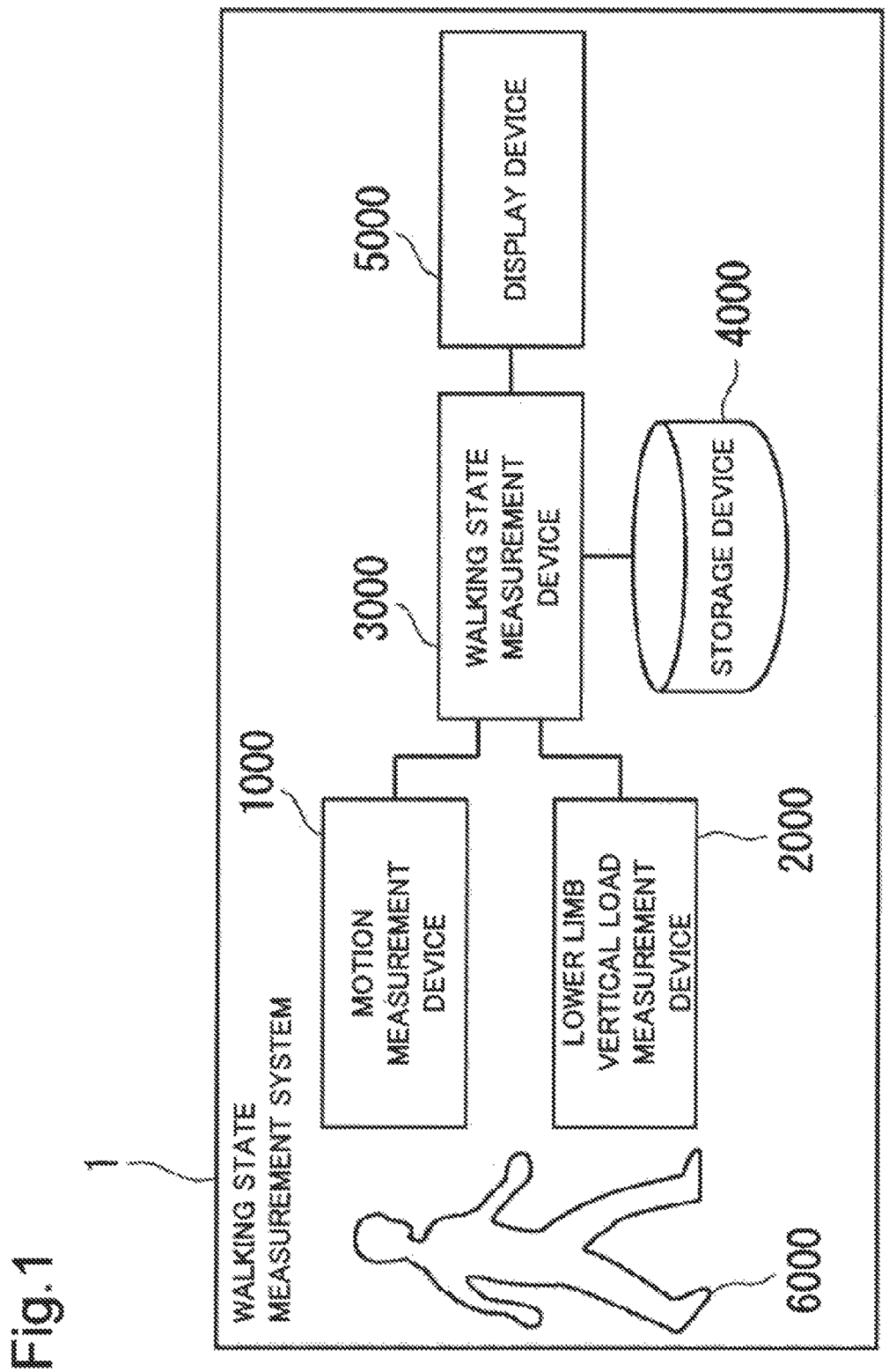
FIG. 1 is a system configuration diagram illustrating a system configuration example of a walking state measurement system according to a first example embodiment of the present invention.

Preferred example embodiments of a walking state measurement device, a walking state measurement system, a walking state measurement method, a walking state measurement program, and a storage medium for storing the walking state measurement program, according to the present invention, will be described below with reference to accompanying drawings. While a walking state measurement device, a walking state measurement system, and a walking state measurement method, according to the present invention, will be described in the following description, it goes without saying that such a walking state measurement method may be implemented as a walking state measurement program executable by a computer, or the walking state measurement program may be recorded in a computer-readable recording medium. Further, it goes without saying that reference signs given to the drawings below are given to components for convenience, as examples for facilitating understanding, and are not intended to limit the present invention to the illustrated aspects.

Characteristic of Present Invention

Prior to description of example embodiments of the present invention, first, an overview of a characteristic of the present invention will be described. A main characteristic of the present invention is to include a floor reaction force estimation means for estimating a floor reaction force by use of at least either of motion data and lower limb vertical load data of a walker, and outputting the floor reaction force as floor reaction force data, and a walking state calculation means for calculating a walking state of the walker by use of at least either of the motion data and the floor reaction force data. Thus, an arrangement position of a sensor reacting to a floor reaction force, such as a pressure sensor, arranged on a surface of a shoe which a walker wears and walks with does not need to be adjusted for each walker.

EXAMPLE EMBODIMENTS OF PRESENT INVENTION

Three (first to third) example embodiments of the present invention will be described in detail below with reference to drawings. In the drawings referred to below, a transmission direction of data or the like is not limited to a direction of an arrow.

First Example Embodiment

First, a first example embodiment of the present invention will be described with reference to drawings.

Description of Configuration

Configuration Example of Walking State Measurement System

A system configuration of a walking state measurement system according to the first example embodiment of the present invention will be described with reference to FIG. 1. FIG. 1 is a system configuration diagram illustrating a system configuration example of the walking state measurement system according to the first example embodiment of the present invention. The walking state measurement system 1 illustrated in FIG. 1 is a system measuring a walking state of a walker 6000.

As illustrated in FIG. 1, the walking state measurement system 1 is configured to include at least a motion measurement device 1000, a lower limb vertical load measurement device 2000, a walking state measurement device 3000, a storage device 4000, and a display device 5000. A connection method between the devices included in the walking state measurement system 1 is not limited to a specific connection method. For example, the devices included in the walking state measurement system 1 may be connected in a wired manner by use of a local area network (LAN) cable, a universal serial bus (USB) cable, or the like, or may be wirelessly connected by use of Bluetooth (registered trademark) or a wireless LAN.

The motion measurement device 1000 is a device measuring a motion of the walker 6000. For example, a motion is information such as an angle and angular velocity of each joint, and an attitude, a position, acceleration, and angular velocity of each segment when the body of the walker 6000 is considered as a rigid body link model, but is not limited to such information, according to the first example embodiment. The motion measurement device 1000 transmits measurement data indicating the measured motion (hereinafter referred to as motion data) of the walker 6000 to the walking state measurement device 3000.

An inertial measurement unit (IMU) including an accelerometer and an angular velocimeter, a smartphone, or the like may be used as an example of the motion measurement device 1000. It is desirable that a measurement range of each of the accelerometer and the angular velocimeter in attached positions include maximum acceleration and maximum angular velocity when the walker 6000 is walking. An optical motion capture device, a goniometer, a camera, and the like may be used as another example of the motion measurement device 1000. However, a specific device as the motion measurement device 1000 according to the first example embodiment is not limited to any of the aforementioned examples.

The motion measurement device 1000 may measure a plurality of motions. Accordingly, a number of motion measurement devices is not limited to one.

Time intervals at which the motion measurement device 1000 measures a motion of the walker 6000 are not particularly limited. However, when the time interval is too long, calculation accuracy of a walking state, to be described later, may decline; and on the other hand, when the time interval is too short, an amount of transmitted data may be too much. Accordingly, considering a walking cycle of the walker 6000, it is desirable that the motion measurement device 1000 measure a motion at, for example, 10-millisecond intervals.

The lower limb vertical load measurement device 2000 is a device measuring a lower limb vertical load of the walker 6000. A lower limb vertical load refers to a total amount of vertical load applied to a sole surface of a left lower limb or a right lower limb of the walker 6000. The lower limb vertical load measurement device 2000 transmits measurement data indicating the measured lower limb vertical load (hereinafter referred to as lower limb vertical load data) to the walking state measurement device 3000.

For example, the lower limb vertical load measurement device 2000 may be considered to be configured by use of at least one sensor having an entire sole surface as a pressure-sensitive surface. For example, as a sensor reacting to a floor reaction force, such as a pressure sensor, arranged on a surface of a shoe which the walker 6000 wears and walks with, the load measurement device described in PTL 2 or a pressure gauge such as a strain gauge type pressure gauge or a capacitance type pressure gauge may be used in order to provide a measurement function of a lower limb vertical load. It is desirable that a measurement range of the sensor include a maximum lower limb vertical load when the walker 6000 is walking.

The lower limb vertical load measurement device 2000 may be installed on either of a left lower limb and a right lower limb, or on each of both lower limbs, and measure a lower limb vertical load in a region where the device is installed.

Time intervals at which the lower limb vertical load measurement device 2000 measures a lower limb vertical load of the walker 6000 is not particularly limited. However, when the time interval is too long, calculation accuracy of a walking state, to be described later, may decline, and on the other hand, when the time interval is too short, an amount of transmitted data may be too much. Accordingly, considering a walking cycle of the walker 6000, it is desirable that the lower limb vertical load measurement device 2000 measure a lower limb vertical load at, for example, 10-millisecond intervals.

The walking state measurement device 3000 receives motion data and lower limb vertical load data from the motion measurement device 1000 and the lower limb vertical load measurement device 2000, respectively. By use of the received motion data and lower limb vertical load data, the walking state measurement device 3000 calculates a walking state of the walker 6000. The walking state measurement device 3000 transmits calculation data indicating the calculated walking state (hereinafter referred to as walking state data) to the display device 5000. For example, a walking state includes indicators such as joint torque, muscle tension, an amount of muscle activity, and a metabolic cost, but is not limited only to such indicators, according to the first example embodiment. A specific functional configuration of the walking state measurement device 3000 will be described separately with a separate drawing.

The storage device 4000 is a device storing designated data required for calculating a walking state of the walker 6000. The storage device 4000 transmits designated data required for calculating a walking state (hereinafter referred to as required calculation data) to the walking state measurement device 3000. While the storage device 4000 is described as a configuration separate from the walking state measurement device 3000, according to the first example embodiment, the present invention is not limited to such a configuration, and for example, the storage device 4000 may be built into the walking state measurement device 3000. Data stored in the storage device 4000 will be described separately with a separate drawing.

The display device 5000 is a device displaying walking state data received from the walking state measurement device 3000. The display device 5000 may display at least one type of data out of motion data, lower limb vertical load data, and data related to a floor reaction force, together with the walking state data.

Configuration Example of Walking State Measurement Device

Figure 2:
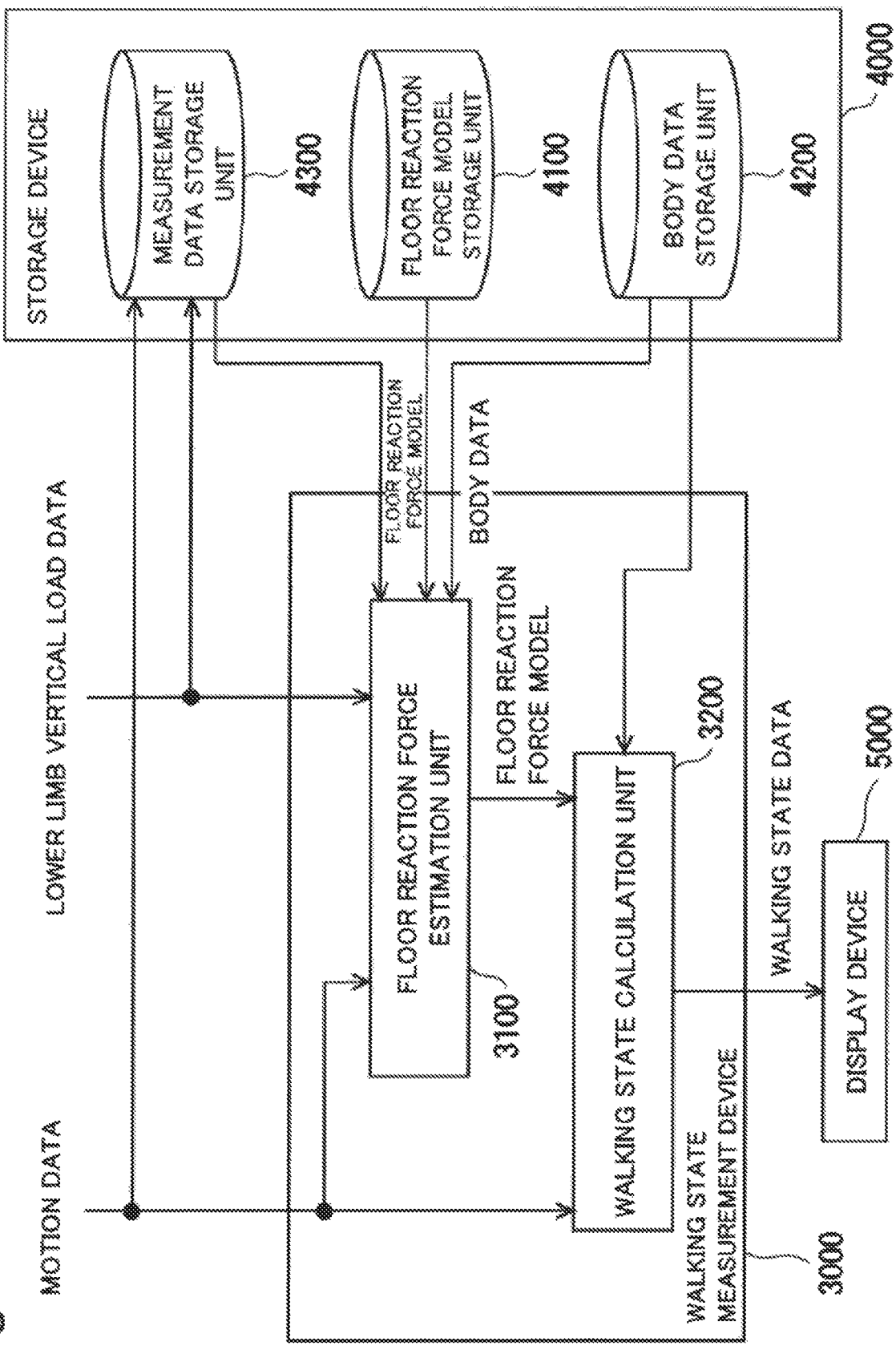
FIG. 2 is a functional block diagram illustrating a functional configuration example of a walking state measurement device in the walking state measurement system according to the first example embodiment of the present invention.

Next, a functional configuration of the walking state measurement device 3000 in the walking state measurement system 1 according to the first example embodiment will be described with reference to FIG. 2. FIG. 2 is a functional block diagram illustrating functional configuration examples of the walking state measurement device 3000 and the storage device 4000 in the walking state measurement system 1 according to the first example embodiment. As illustrated in FIG. 2, the walking state measurement device 3000 is configured to include at least a floor reaction force estimation unit 3100 and a walking state calculation unit 3200.

Floor Reaction Force Estimation Unit 3100

The floor reaction force estimation unit 3100 in the walking state measurement device 3000 receives motion data and lower limb vertical load data from the motion measurement device 1000 and the lower limb vertical load measurement device 2000, respectively. Next, the floor reaction force estimation unit 3100 receiving the motion data and the lower limb vertical load data refers to a body data storage unit 4200, to be described later, in the storage device 4000 and acquires body data of the walker 6000 stored in the body data storage unit 4200.

Subsequently, the floor reaction force estimation unit 3100 refers to a floor reaction force model storage unit 4100, to be described later, in the storage device 4000 and acquires a designated floor reaction force model (for example, a previously designated floor reaction force model) stored in the floor reaction force model storage unit 4100. Then, in accordance with the acquired floor reaction force model, the floor reaction force estimation unit 3100 estimates a floor reaction force by use of at least either of the received motion data and the received lower limb vertical load data, and the previously acquired body data. The floor reaction force estimation unit 3100 transmits the estimated floor reaction force to the walking state calculation unit 3200 as floor reaction force data.

A floor reaction force refers to characteristics of a force received by a sole surface from the floor, such as three component forces (a vertical component force, a lateral component force, and a longitudinal component force) of the force received by the sole surface from the floor, a point of application of floor reaction force (coordinate values on the floor surface), and also a rotational moment indicating a rotation strength of the force. The floor reaction force estimated by the floor reaction force estimation unit 3100 is not limited to one type out of the characteristics of the force received from the floor. The floor reaction force estimation unit 3100 may estimate a plurality of types of characteristics.

The floor reaction force estimation unit 3100 receives, from the motion measurement device 1000, attitude information about each segment when the body of the walker 6000 is considered as a rigid body link model, and uses the received attitude information as the motion data when estimating a floor reaction force. In such a case, the floor reaction force estimation unit 3100 may use, as the motion data, attitude information about at least one of a thigh region, a lower leg region, and a foot region of the walker 6000 in the attitude information about each segment. Alternatively, the floor reaction force estimation unit 3100 may receive, from the motion measurement device 1000, at least either of acceleration and angular velocity of each segment when the body of the walker 6000 is considered as a rigid body link model, and use at least either of the received acceleration and the received angular velocity as the motion data when estimating a floor reaction force.

Walking State Calculation Unit 3200

The walking state calculation unit 3200 receives motion data and floor reaction force data from the motion measurement device 1000 and the floor reaction force estimation unit 3100, respectively. Next, the walking state calculation unit 3200 refers to the body data storage unit 4200, to be described later in the storage device 4000 and acquires body data of the walker 6000 stored in the body data storage unit 4200.

Subsequently, the walking state calculation unit 3200 calculates a walking state of the walker 6000 by use of at least either of the received motion data and the received floor reaction force data, and the acquired body data. Specifically, the walking state calculation unit 3200 calculates at least either of joint torque and muscle tension as a walking state of the walker 6000, based on inverse dynamic calculation. The walking state calculation unit 3200 supplies the calculated walking state of the walker 6000 to the display device 5000 as walking state data.

Configuration Example of Storage Device

Next, a functional configuration of the storage device 4000 in the walking state measurement system 1 according to the first example embodiment of the present invention will be described with reference to FIG. 2. As illustrated in FIG. 2, the storage device 4000 includes at least the floor reaction force model storage unit 4100, the body data storage unit 4200, and a measurement data storage unit 4300.

Floor Reaction Force Model Storage Unit 4100

The floor reaction force model storage unit 4100 stores a previously designated floor reaction force model. A designated floor reaction force model refers to a model indicating a correlation between a floor reaction force, and a motion and a lower limb vertical load of the walker 6000. For example, a physical model based on a dynamic characteristic of a body may be considered as a floor reaction force model. In addition, a table indicating a correspondence relation between a floor reaction force, and a motion and a lower limb vertical load of the walker, a regression model (such as linear regression, the k-nearest neighbors algorithm, a neural network, and support vector regression) and a coefficient thereof, and the like may be considered as a floor reaction force model. However, a floor reaction force model according to the first example embodiment is not limited to the models described above.

Body Data Storage Unit 4200

The body data storage unit 4200 stores body data of the walker 6000. Body data include a height and a weight of the walker 6000, a length, a weight, and a moment of inertia of each segment.

Measurement Data Storage Unit 4300

The measurement data storage unit 4300 stores at least motion data and lower limb vertical load data measured by the motion measurement device 1000 and the lower limb vertical load measurement device 2000, respectively.

Description of Operation

Figure 3:
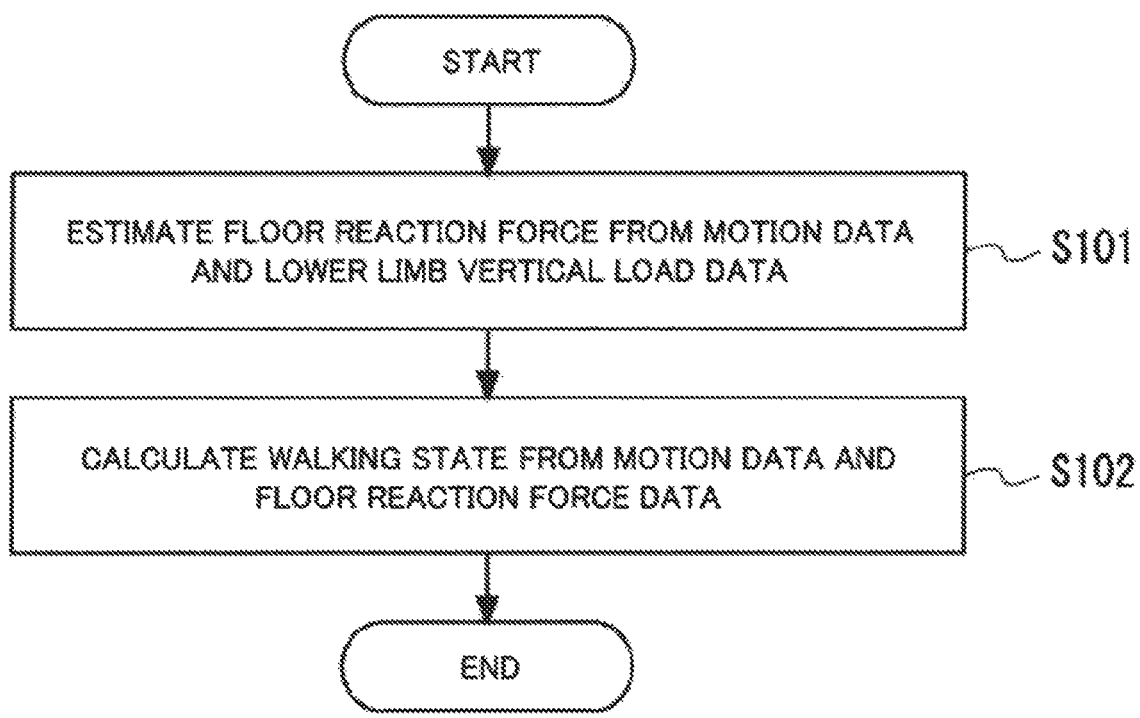
FIG. 3 is a flowchart illustrating an example of a flow of walking state measurement processing in the walking state measurement device in the walking state measurement system according to the first example embodiment of the present invention.

Next, an example of an operation of the walking state measurement device 3000 in the walking state measurement system 1 according to the first example embodiment illustrated in FIG. 1 will be described with reference to FIG. 3. FIG. 3 is a flowchart illustrating an example of a flow of walking state measurement processing in the walking state measurement device 3000 in the walking state measurement system 1 according to the first example embodiment.

In the flowchart illustrated in FIG. 3, first, the floor reaction force estimation unit 3100 estimates a floor reaction force in accordance with a designated floor reaction force model stored in the floor reaction force model storage unit 4100, by use of at least either of motion data transmitted from the motion measurement device 1000 and lower limb vertical load measurement data transmitted from the lower limb vertical load measurement device 2000, and outputs the estimated floor reaction force as floor reaction force data (Step S101).

Next, the walking state calculation unit 3200 calculates a walking state of the walker 6000 by use of at least either of the motion data transmitted from the motion measurement device 1000 and the floor reaction force data output from the floor reaction force estimation unit 3100 in Step S101 (Step S102).

By performing the processing Steps S101 and S102 described above, the walking state measurement device 3000 in the walking state measurement system 1 according to the first example embodiment can measure a walking state of the walker 6000.

Description of Effect of First Example Embodiment

As described above, the walking state measurement system 1 according to the first example embodiment can provide an effect that adjustment of an arrangement position of a sensor reacting to a floor reaction force, such as a pressure sensor, arranged on a surface of a shoe which a walker wears and walks with becomes unnecessary. The reason is that the walking state measurement device 3000 in the walking state measurement system 1 according to the first example embodiment includes the floor reaction force estimation unit 3100 having a function of estimating a floor reaction force, based on two types of measurement data being motion data and lower limb vertical load data of a target (walker 6000). A lower limb vertical load may be measured independently of a size and a shape of a foot of the target (walker 6000) without adjusting an arrangement position of a sensor, by use of, for example, the technology described in PTL 2, or the like.

Furthermore, at least one sensor reacting to a floor reaction force has only to be required for measurement of the lower limb vertical load, and therefore an effect that the walking state measurement device 3000 can be provided with a simple and inexpensive configuration can be provided at the same time.

Second Example Embodiment

Next, a second example embodiment of the invention will be described with reference to drawings. For convenience of description, a component having the same function as a component included in a drawing described in the aforementioned first example embodiment is given the same sign, and overlapping description is omitted.

Description of Configuration

Configuration Example of Walking State Measurement System

Figure 4:
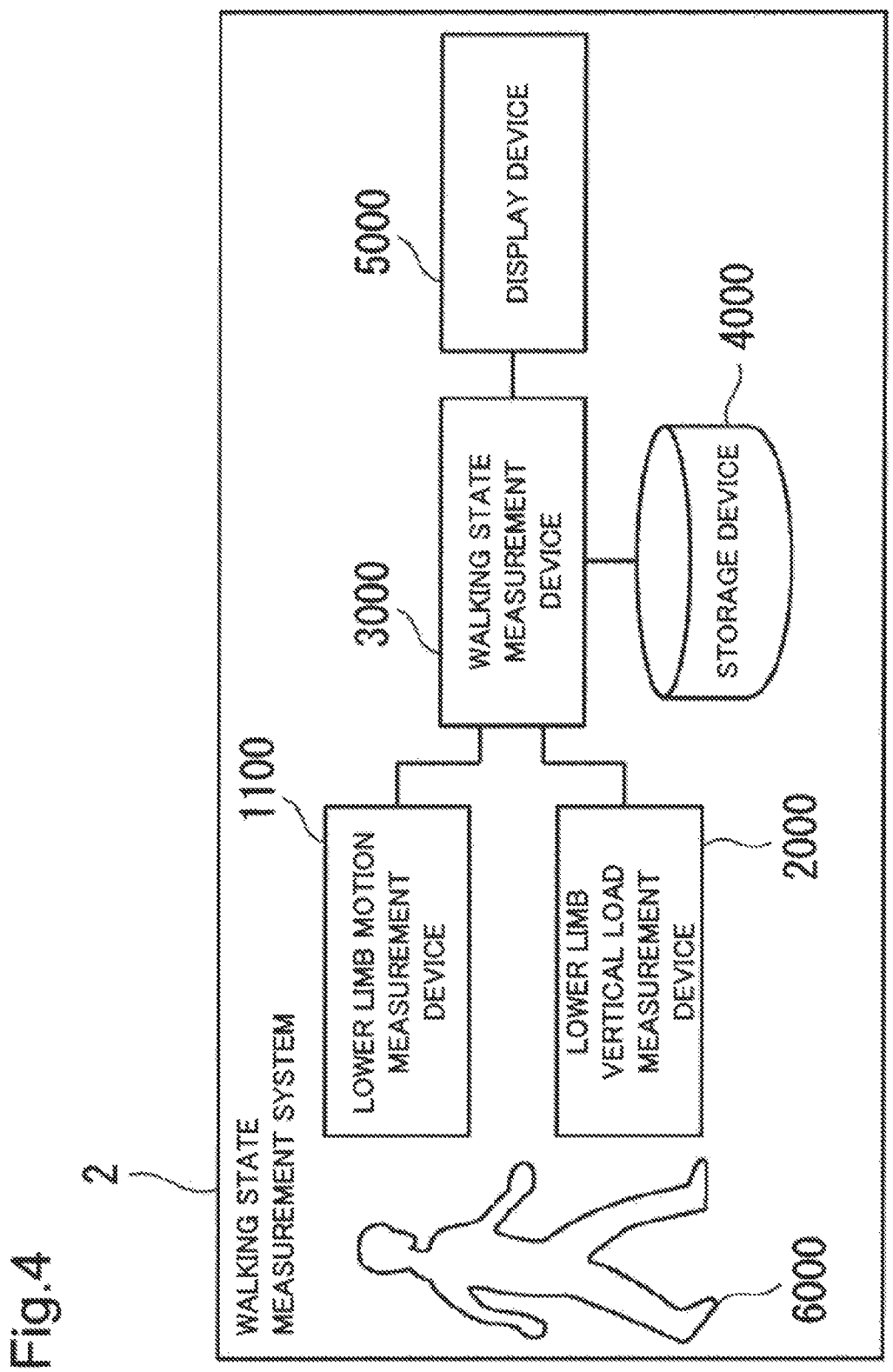
FIG. 4 is a system configuration diagram illustrating a system configuration example of a walking state measurement system according to a second example embodiment of the present invention.

A system configuration of a walking state measurement system according to the second example embodiment of the invention will be described with reference to FIG. 4. FIG. 4 is a system configuration diagram illustrating a system configuration example of the walking state measurement system according to the second example embodiment of the invention. The walking state measurement system 2 illustrated in FIG. 4 is a system measuring a walking state of a walker 6000.

As illustrated in FIG. 4, the walking state measurement system 2 is configured to include at least a lower limb motion measurement device 1100, a lower limb vertical load measurement device 2000, a walking state measurement device 3000, a storage device 4000, and a display device 5000. The difference between the walking state measurement system 1 illustrated in FIG. 1 as the first example embodiment and the walking state measurement system 2 illustrated in FIG. 4 as the second example embodiment is that the motion measurement device 1000 in FIG. 1 is replaced by a lower limb motion measurement device 1100 in FIG. 4.

The lower limb motion measurement device 1100 measures attitude information about each of six segments being the left thigh, the left lower leg, the left foot region, the right thigh, the right lower leg, and the right foot region when the body of the walker 6000 is considered as a rigid body link model. Then, the lower limb motion measurement device 1100 outputs data related to the measured attitude information to the walking state measurement device 3000 as motion data.

Configuration Example of Lower Limb Motion Measurement Device

Figure 5:
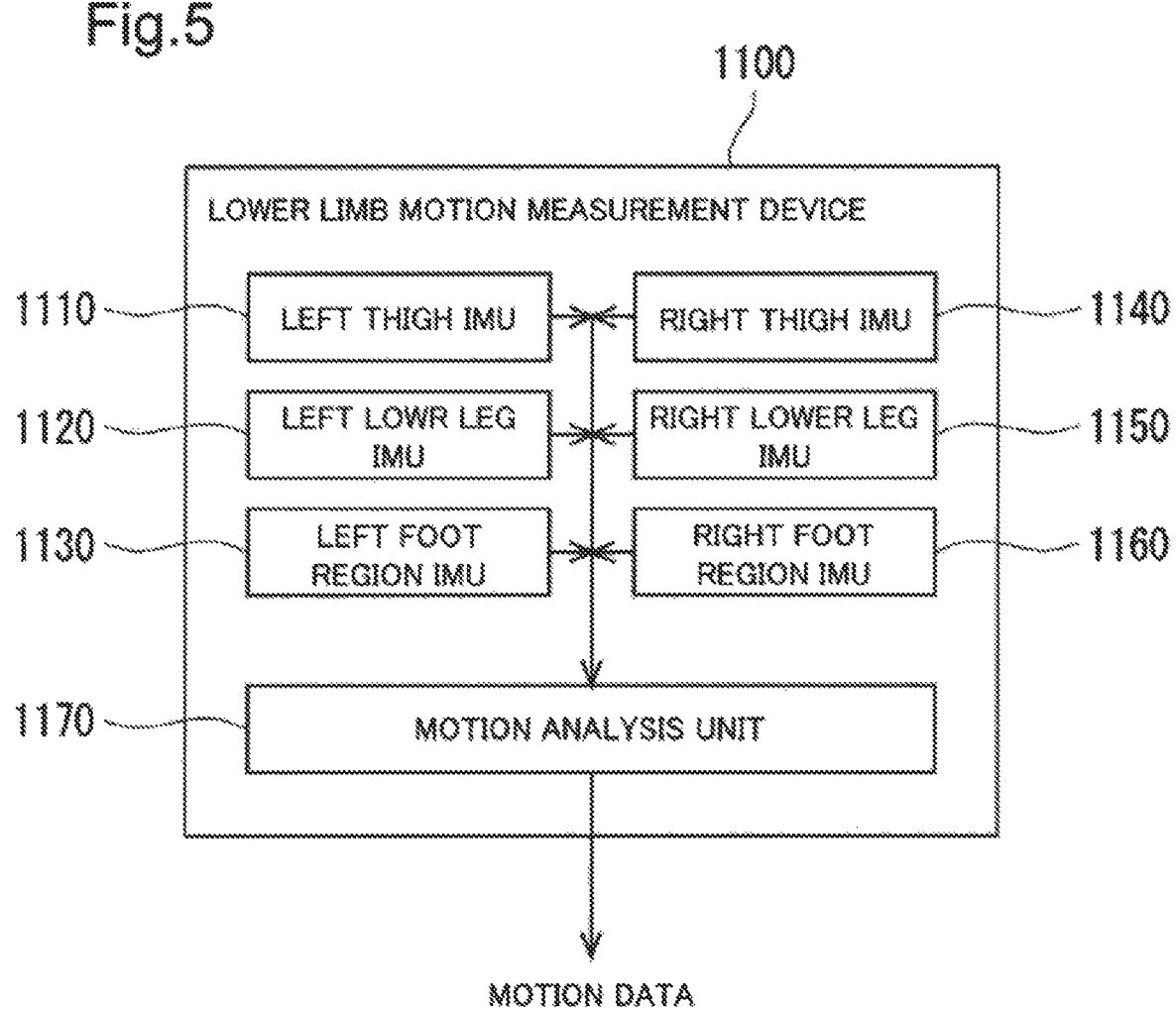
FIG. 5 is a functional block diagram illustrating a functional configuration example of a lower limb motion measurement device in the walking state measurement system according to the second example embodiment of the present invention.

Next, a functional configuration of the lower limb motion measurement device 1100 in the walking state measurement system 1 according to the second example embodiment will be described with reference to FIG. 5. FIG. 5 is a functional block diagram illustrating a functional configuration example of the lower limb motion measurement device 1100 in the walking state measurement system 2 according to the second example embodiment. As illustrated in FIG. 5, the lower limb motion measurement device 1100 is configured to include at least a left thigh inertial measurement unit (IMU) 1110, a left lower leg IMU 1120, a left foot region IMU 1130, a right thigh IMU 1140, a right lower leg IMU 1150, a right foot region IMU 1160, and a motion analysis unit 1170.

The left thigh IMU 1110, the left lower leg IMU 1120, the left foot region IMU 1130, the right thigh IMU 1140, the right lower leg IMU 1150, and the right foot region IMU 1160 measure acceleration and angular velocity at the segments being the left thigh, the left lower leg, the left foot region, the right thigh, the right lower leg, and the right foot region, respectively.

With regard to an attachment position of each of the left thigh IMU 1110, the left lower leg IMU 1120, the left foot region IMU 1130, the right thigh IMU 1140, the right lower leg IMU 1150, and the right foot region IMU 1160, it is desirable that, for example, when measurements are made in the foot regions, the left foot region IMU 1130 and the right foot region IMU 1160 are attached to the insteps of the walker 6000, respectively.

As examples of attachment positions of the other IMUs, when an attitude of a thigh region or a lower leg region is to be measured, since a change in an attachment position on the thigh or the lower leg in a longitudinal direction does not affect measurement of the attitude, each of the left thigh IMU 1110, the right thigh IMU 1140, the left lower leg IMU 1120, and the right lower leg IMU 1150 may be attached to any position on the thigh or the lower leg.

It is assumed that an attachment position of each of the left thigh IMU 1110, the left lower leg IMU 1120, the left foot region IMU 1130, the right thigh IMU 1140, the right lower leg IMU 1150, and the right foot region IMU 1160 is thus attached in a suitable position, based on a segment where each IMU makes a measurement.

The motion analysis unit 1170 included in the lower limb motion measurement device 1100 receives acceleration and angular velocity at each segment from each of the left thigh IMU 1110, the left lower leg IMU 1120, the left foot region IMU 1130, the right thigh IMU 1140, the right lower leg IMU 1150, and the right foot region IMU 1160.

Next, the motion analysis unit 1170 calculates an attitude of each segment by use of the received acceleration and angular velocity. An attitude refers to a rotation matrix or a quaternion based on designated standard coordinates. A calculation method of an attitude of each segment is not particularly limited, and a common method may be used; and therefore detailed description is omitted. As a common method, for example, a method of calculating an attitude by use of gravitational acceleration and an integrated value of angular velocity is known.

Finally, the motion analysis unit 1170 outputs the calculation result being data indicating an attitude of each of the segments being the left thigh, the left lower leg, the left foot region, the right thigh, the right lower leg, and the right foot region to the walking state measurement device 3000 as motion data. In other words, the motion analysis unit 1170 outputs attitude information about each segment when the body of the walker 6000 is considered as a rigid body link model to the walking state measurement device 3000 as motion data. In such a case, the motion analysis unit 1170 may output attitude information about at least one of the thigh regions and the lower leg regions of the walker 6000 in the attitude information about each segment to the walking state measurement device 3000 as motion data. Alternatively, the motion analysis unit 1170 may output at least either of acceleration and angular velocity of each segment when the body of the walker 6000 is considered as a rigid body link model to the walking state measurement device 3000 as motion data.

Configuration Example of Walking State Measurement Device

Next, a functional configuration of the walking state measurement device 3000 in the walking state measurement system 2 according to the second example embodiment will be described. The walking state measurement device 3000 in the walking state measurement system 2 according to the second example embodiment has a functional configuration similar to that according to the first example embodiment illustrated in FIG. 2 and is configured to include at least a floor reaction force estimation unit 3100 and a walking state calculation unit 3200.

Floor Reaction Force Estimation Unit 3100

The floor reaction force estimation unit 3100 in the walking state measurement device 3000 receives motion data and lower limb vertical load data from the lower limb motion measurement device 1100 and the lower limb vertical load measurement device 2000, respectively. Next, the floor reaction force estimation unit 3100 receiving the motion data and the lower limb vertical load data refers to a body data storage unit 4200 in the storage device 4000 illustrated in FIG. 2 and acquires a length Lfoot of the foot region of the walker 6000 stored in the body data storage unit 4200.

Subsequently, the floor reaction force estimation unit 3100 refers to a floor reaction force model storage unit 4100 in the storage device 4000 illustrated in FIG. 2 and acquires a designated floor reaction force model (for example, a previously designated floor reaction force model) stored in the floor reaction force model storage unit 4100. Then, in accordance with the acquired floor reaction force model, the floor reaction force estimation unit 3100 estimates a floor reaction force by use of at least either of the received motion data and the received lower limb vertical load data, and the previously acquired length Lfoot of the foot region, and transmits the estimated floor reaction force to the walking state calculation unit 3200 as floor reaction force data.

The floor reaction force estimation unit 3100 estimates a floor reaction force, based on a procedure as exemplified below. First, equation (1) below is an example of a floor reaction force model for calculating a three-dimensional vector GRF having three component forces (a vertical component force, a lateral component force, and a longitudinal component force) of a floor reaction force as components and coordinates CoP of a point of application of floor reaction force on the sole surface.

[Math. 1]

$$\overrightarrow{GRF}(t) = \alpha(t) \cdot x(t) + \beta(t) \cdot y(t) + \gamma(t) \\ \overrightarrow{CoP}(t) = \kappa(t) \cdot x(t) + \lambda(t) \cdot y(t) + \mu(t) \quad \quad (1)$$

where
$t \in Z$: walking cycle (0 to 100%)
$\overrightarrow{GRF}(t) \in R^{3 \times 1}$: unit vector of GRF
$\overrightarrow{CoP}(t) \in R^{2 \times 1}$: unit vector of CoP
$x(t) \in R^{3 \times 1}$: attitude of thigh region
$y(t) \in R^{3 \times 1}$: attitude of lower leg region
$\alpha(t), \beta(t) \in R^{3 \times 3}, \gamma(t) \in R^{3 \times 1}$: partial regression coefficient
$\kappa(t), \lambda(t) \in R^{2 \times 3}, \mu(t) \in R^{2 \times 1}$: partial regression coefficient The floor reaction force model indicated in equation (1) is a linear regression equation indicating a correlation between an attitude x of the thigh region, an attitude y of the lower leg region, and a unit vector of a three-dimensional vector GRF related to three component forces of a floor reaction force $$\overrightarrow{GRF} \quad \quad [\text{Math. 2}]$$

and a unit vector of a two-dimensional vector CoP denoting coordinates of a point of application of floor reaction force on the sole surface $$\overrightarrow{CoP} \quad \quad [\text{Math. 3}]$$

In equation (1), a three-dimensional vector x(t) denotes an attitude of the thigh region, and a three-dimensional vector y(t) denotes an attitude of the lower leg region. Each of 3×3 matrices α(t) and β(t), a three-dimensional vector γ(t), 2×3 matrices κ(t) and λ(t), and a two-dimensional vector μ(t) denotes a partial regression coefficient.

Furthermore, t denotes a walking cycle and takes an integer value in a range from 0 to 100. A walking cycle is a value defined on the basis of a motion of a lower limb and indicates a time point of a cyclic operation of a walk. Typically, t is defined in such a way that t at a time point when the heel of the left lower limb (or the right lower limb) contacts the ground is set to 0, and t at a time point when the toe of the left lower limb (or the right lower limb) leaves the ground is set to 100. Typically, t is defined in such a way that t at a time point when the heel of the left lower limb (or the right lower limb) contacts the ground is set to 0, and t at a next time point when the heel of the left lower limb (or the right lower limb) contacts the ground is set to 100. A method of calculating a walking cycle t by the floor reaction force estimation unit 3100 is a common method and is not limited to a specific method. For example, the floor reaction force estimation unit 3100 may use a method of referring to the measurement data storage unit 4300, determining a timing of the heel of the left lower limb (or the right lower limb) contacting the ground and a timing of the toe leaving the ground from past motion data and a lower limb vertical load, dividing the time between the timing of the heel contacting the ground and the timing of the toe leaving the ground into 100 equal parts, and defining the timing of the heel contacting the ground and the timing of the toe leaving the ground as a walking cycle 0 to 100. A method of determining timings of the heel of the left lower limb (or right lower limb) contacting the ground, dividing a time between adjacent timings of the heel contacting the ground into 100 equal parts, and defining the timings of the heel contacting the ground and acquired times as a walking cycle 0 to 100 may be used.

By substituting the attitude x of the thigh region and the attitude y of the lower leg region received as motion data into equation (1), a unit vector of the three-dimensional vector of the floor reaction force $$\overrightarrow{GRF} \quad \quad [\text{Math. 4}]$$

and a unit vector of the coordinates CoP of the point of application of floor reaction force $$\overrightarrow{CoP} \quad \quad [\text{Math. 5}]$$

are calculated by the floor reaction force estimation unit 3100.

Next, by substituting received lower limb vertical load measurement data Pfoot into equation (2) below, the floor reaction force estimation unit 3100 calculates the three-dimensional vector GRF having the three component forces of the floor reaction force as components.

[Math. 6]

$$GRF = \frac{P_{foot}}{GRF_z} \times \overrightarrow{GRF} \quad \quad (2)$$

where
$GRF_z$: magnitude of vertical component force out of 3 component forces of floor reaction force Subsequently, by substituting the length Lfoot of the foot region of the walker 6000 into equation (3) below, the floor reaction force estimation unit 3100 calculates the two-dimensional vector CoP having coordinate components of the point of application of floor reaction force on the sole surface.

[Math. 7]

$$CoP = L_{foot} \times \overrightarrow{CoP} \quad \quad (3)$$

As described above, the floor reaction force estimation unit 3100 estimates a floor reaction force (a floor reaction force GRF composed of three component forces, and coordinates CoP of a point of application of floor reaction force) and transmits the estimated floor reaction force to the walking state calculation unit 3200 as floor reaction force data.

The walking state calculation unit 3200 receiving motion data and floor reaction force data from the lower limb motion measurement device 1100 and the floor reaction force estimation unit 3100, respectively, calculates a walking state of the walker 6000 in accordance with a procedure similar to that according to the first example embodiment and supplies the calculated walking state to the display device 5000 as walking state data.

Description of Effect of Second Example Embodiment

As described above, the walking state measurement system 2 according to the second example embodiment can provide an effect that adjustment of an arrangement position of a sensor reacting to a floor reaction force, such as a pressure sensor, arranged on a surface of a shoe which a walker wears and walks with becomes unnecessary, similarly to the walking state measurement system 1 according to the aforementioned first example embodiment. The reason is that, similarly to the walking state measurement system 1 according to the first example embodiment, the walking state measurement device 3000 in the walking state measurement system 2 according to the second example embodiment also includes the floor reaction force estimation unit 3100 estimating a floor reaction force, based on two types of measurement data being motion data and lower limb vertical load data of a target (walker 6000).

Furthermore, the walking state measurement system 2 according to the second example embodiment also can provide an effect that, since each of the left thigh IMU 1110, the left lower leg IMU 1120, the left foot region IMU 1130, the right thigh IMU 1140, the right lower leg IMU 1150, and the right foot region IMU 1160 in the lower limb motion measurement device 1100 may be attached in any position on a segment in a longitudinal direction, equipping becomes easy. The reason is that a change in an attachment position on each segment in a longitudinal direction does not affect measurement of an attitude.

Third Example Embodiment

Next, a third example embodiment of the present invention will be described with reference to drawings. For convenience of description, a component having the same function as a component included in a drawing described in the aforementioned first and second example embodiments is given the same sign, and overlapping description is omitted.

Description of Configuration

Configuration Example of Walking State Measurement System

Figure 6:
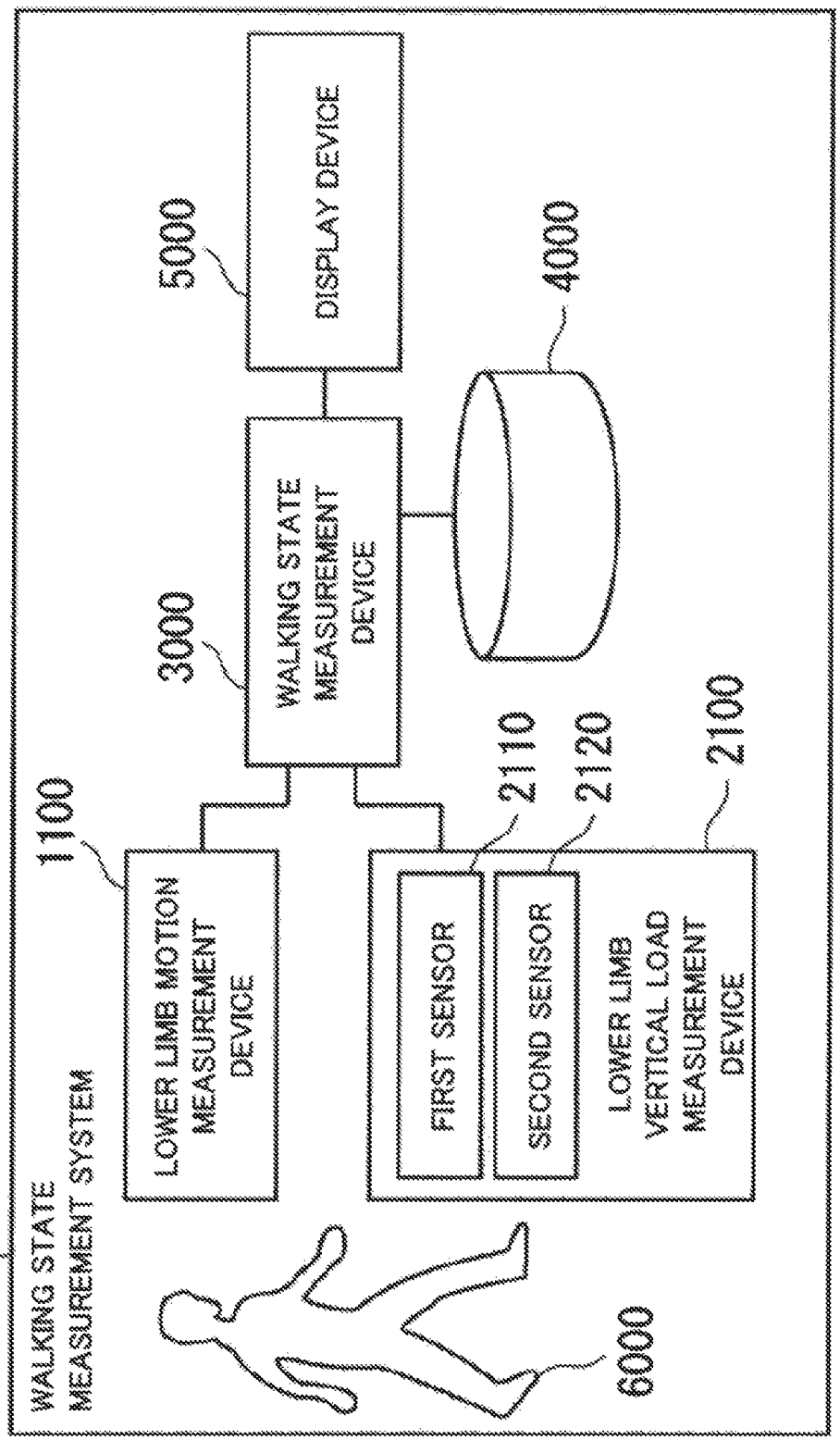
FIG. 6 is a system configuration diagram illustrating a system configuration example of a walking state measurement system according to a third example embodiment of the present invention.

A system configuration of a walking state measurement system according to the third example embodiment of the present invention will be described with reference to FIG. 6. FIG. 6 is a system configuration diagram illustrating a system configuration example of the walking state measurement system according to the third example embodiment of the present invention. The walking state measurement system 3 illustrated in FIG. 6 is a system measuring a walking state of a walker 6000.

As illustrated in FIG. 6, the walking state measurement system 3 is configured to include at least a lower limb motion measurement device 1100, a lower limb vertical load measurement device 2100, a walking state measurement device 3000, a storage device 4000, and a display device 5000. While FIG. 6 illustrates a configuration using the lower limb motion measurement device 1100 similar to that according to the second example embodiment in FIG. 4, the walking state measurement system 3 may be configured by use of a motion measurement device 1000 similar to that according to the first example embodiment in FIG. 1 in place of the lower limb motion measurement device 1100. The difference between the walking state measurement systems 1 and 2 illustrated in FIGS. 1 and 4 as the first and second example embodiments, and the walking state measurement system 3 illustrated in FIG. 6 as the third example embodiment is that the lower limb vertical load measurement device 2000 in FIGS. 1 and 2 is replaced by the lower limb vertical load measurement device 2100 including two sensors in FIG. 6. The lower limb vertical load measurement device 2100 also differs from the walking state measurement systems 1 and 2 illustrated in FIGS. 1 and 2 in including a first sensor 2110 and a second sensor 2120, and outputting two types of lower limb vertical load data to the walking state measurement device 3000.

Configuration Example of Lower Limb Vertical Load Measurement Device

As described above, the lower limb vertical load measurement device 2100 includes at least two sensors being the first sensor 2110 and the second sensor 2120. Each of the two sensors being the first sensor 2110 and the second sensor 2120 measures a lower limb vertical load in each area acquired by dividing an entire area of a sole surface into two areas, based on a preset designated standard. For example, a configuration of the first sensor 2110 and the second sensor 2120 measuring lower limb vertical loads in two areas being the toe side and the heel side of the sole surface, respectively, may be considered. Then, the lower limb vertical load measurement device 2100 transmits lower limb vertical loads measured by the sensors being the first sensor 2110 and the second sensor 2120 to the walking state measurement device 3000 as first lower limb vertical load data and second lower limb vertical load data, respectively.

Configuration Example of Walking State Measurement Device

Figure 7:
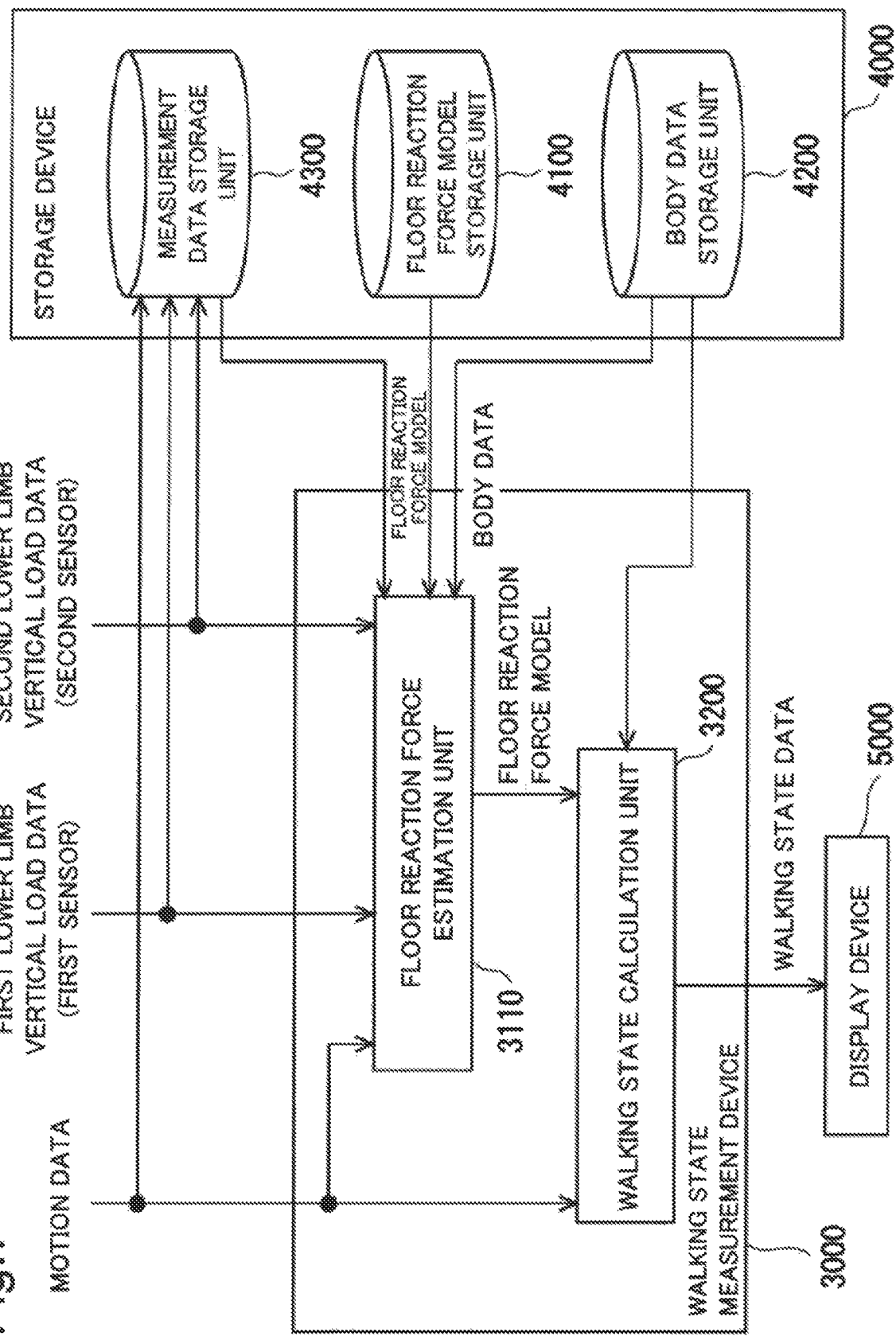
FIG. 7 is a functional block diagram illustrating a functional configuration example of a walking state measurement device in the walking state measurement system according to the third example embodiment of the present invention.

Next, a functional configuration of the walking state measurement device 3000 in the walking state measurement system 3 according to the third example embodiment will be described with reference to FIG. 7. FIG. 7 is a functional block diagram illustrating functional configuration examples of the walking state measurement device 3000 and the storage device 4000 in the walking state measurement system 3 according to the third example embodiment. As illustrated in FIG. 7, the walking state measurement device 3000 is configured to include at least a floor reaction force estimation unit 3110 and a walking state calculation unit 3200. The walking state measurement device 3000 illustrated in FIG. 7 is configured by use of the floor reaction force estimation unit 3110 in place of the floor reaction force estimation unit 3100 in the walking state measurement device 3000 according to the first example embodiment illustrated in FIG. 2.

Floor Reaction Force Estimation Unit 3110

The floor reaction force estimation unit 3110 according to the third example embodiment receives motion data, and first lower limb vertical load data and second lower limb vertical load data from the lower limb motion measurement device 1100 and the lower limb vertical load measurement device 2100, respectively. Specifically, with regard to lower limb vertical load data from the lower limb vertical load measurement device 2100, the floor reaction force estimation unit 3110 receives first lower limb vertical load data measured by the first sensor 2110 and second lower limb vertical load data measured by the second sensor 2120 being two types of lower limb vertical load data in respective areas acquired by dividing the sole surface into two areas.

Next, the floor reaction force estimation unit 3110 receiving the motion data and the two types of lower limb vertical load data calculates lower limb vertical load data Pfoot by adding the received first lower limb vertical load data to the received second lower limb vertical load data. The floor reaction force estimation unit 3110 thereafter estimates a floor reaction force GRF composed of three component forces and coordinates CoP of a point of application of floor reaction force in accordance with a procedure similar to that according to the second example embodiment.

Furthermore, the floor reaction force estimation unit 3110 according to the third example embodiment calculates a ratio R related to the received first lower limb vertical load data and second lower limb vertical load data. The ratio R includes information about a load balance of the sole surface. For example, the ratio R may be a ratio between the first lower limb vertical load data or the second lower limb vertical load data, and the lower limb vertical load data Pfoot. For example, R=1.0 when a load is placed on the toe side, R=0.0 when a load is placed on the heel side, and R=0.5 when a load is equally placed on the toe side and the heel side.

In other words, the floor reaction force estimation unit 3110 according to the third example embodiment estimates a floor reaction force by further using the ratio R related to the received first lower limb vertical load data and second lower limb vertical load data in addition to the estimation processing related to a floor reaction force by the floor reaction force estimation unit 3100 according to the second example embodiment. Subsequently, the floor reaction force estimation unit 3110 transmits the estimated floor reaction force to the walking state calculation unit 3200 as floor reaction force data.

The walking state calculation unit 3200 receiving motion data and floor reaction force data from the lower limb motion measurement device 1100 and the floor reaction force estimation unit 3110, respectively, calculates a walking state of the walker 6000 in accordance with a procedure similar to that according to the first and second example embodiments and supplies the calculated walking state to the display device 5000 as walking state data.

Description of Effect of Third Example Embodiment

As described above, the walking state measurement system 3 according to the third example embodiment provides an effect that adjustment of an arrangement position of a sensor reacting to a floor reaction force, such as a pressure sensor, arranged on a surface of a shoe which a walker wears and walks with becomes unnecessary, similarly to the walking state measurement systems 1 and 2 according to the aforementioned first and second example embodiments. The reason is that the walking state measurement device 3000 in the walking state measurement system 3 according to the third example embodiment also includes the floor reaction force estimation unit 3100 having a function of estimating a floor reaction force, based on two types of measurement data being motion data and lower limb vertical load data of a target (walker 6000).

Furthermore, the walking state measurement system 3 according to the third example embodiment can also provide an effect of being able to more accurately calculate a walking state of the walker 6000. The reason is that addition and use of information about a load balance of the sole surface (that is, information about a ratio R related to first lower limb vertical load data and second lower limb vertical load data) is enabled, and therefore estimation accuracy of a floor reaction force can be improved.

Specifically, for example, in a walk on a slope or a stairway, a configuration of dividing the sole surface into two areas being the toe side and the heel side is effective in terms of lower limb vertical load data. When walking on a slope or a stairway, the walker 6000 tends to adjust a balance by minutely shifting a load backward and forward on the sole surface, in order to prevent a fall. Compared with the walking state measurement device 3000 according to the first and second example embodiments, the walking state measurement device 3000 according to the third example embodiment further enables use of information about a load balance of the sole surface and therefore can more accurately estimate a floor reaction force and consequently more accurately measure a walking state.

Furthermore, in a case of walking in a curve, a configuration of dividing the sole surface into two areas being the outside and the inside of the body is effective in terms of lower limb vertical load data. The reason is that when walking in a curve, the walker 6000 tends to adjust a balance by minutely shifting a load leftward and rightward on the sole surface and changing directions.

Fourth Example Embodiment

Next, a fourth example embodiment of the present invention will be described with reference to drawings.
Description of Configuration FIG. 10 is a functional block diagram illustrating a functional configuration example of a walking state measurement device 3000 according to the fourth example embodiment of the present invention.

Figure 10:
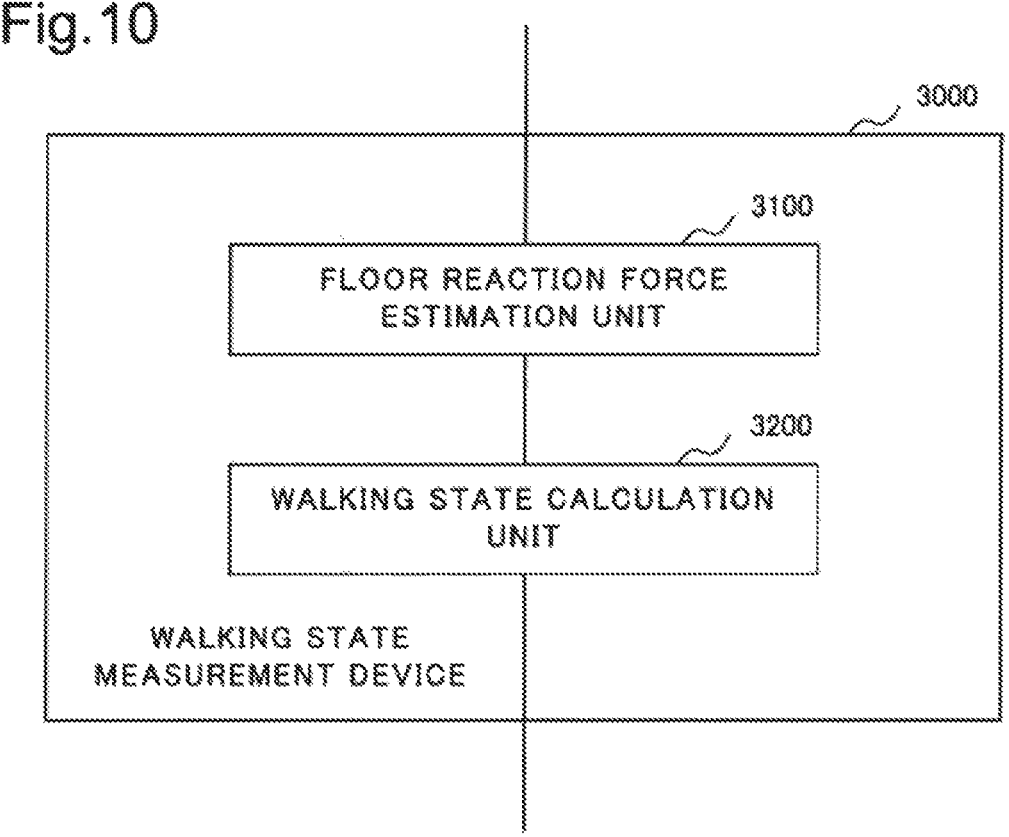
FIG. 10 is a functional block diagram illustrating a functional configuration example of a walking state measurement device according to a fourth example embodiment of the present invention.

As illustrated in FIG. 10, the walking state measurement device 3000 according to the fourth example embodiment includes a floor reaction force estimation unit 3100 and a walking state calculation unit 3200. The floor reaction force estimation unit 3100 estimates a floor reaction force by use of at least either of motion data and lower limb vertical load data of a walker, and outputs the estimated floor reaction force as floor reaction force data. The walking state calculation unit 3200 calculates a walking state of the walker by use of at least either of motion data and floor reaction force data, and outputs the walking state.
Description of Operation FIG. 11 is a flowchart illustrating an operation example of the walking state measurement device according to the fourth example embodiment of the present invention.

Figure 11:
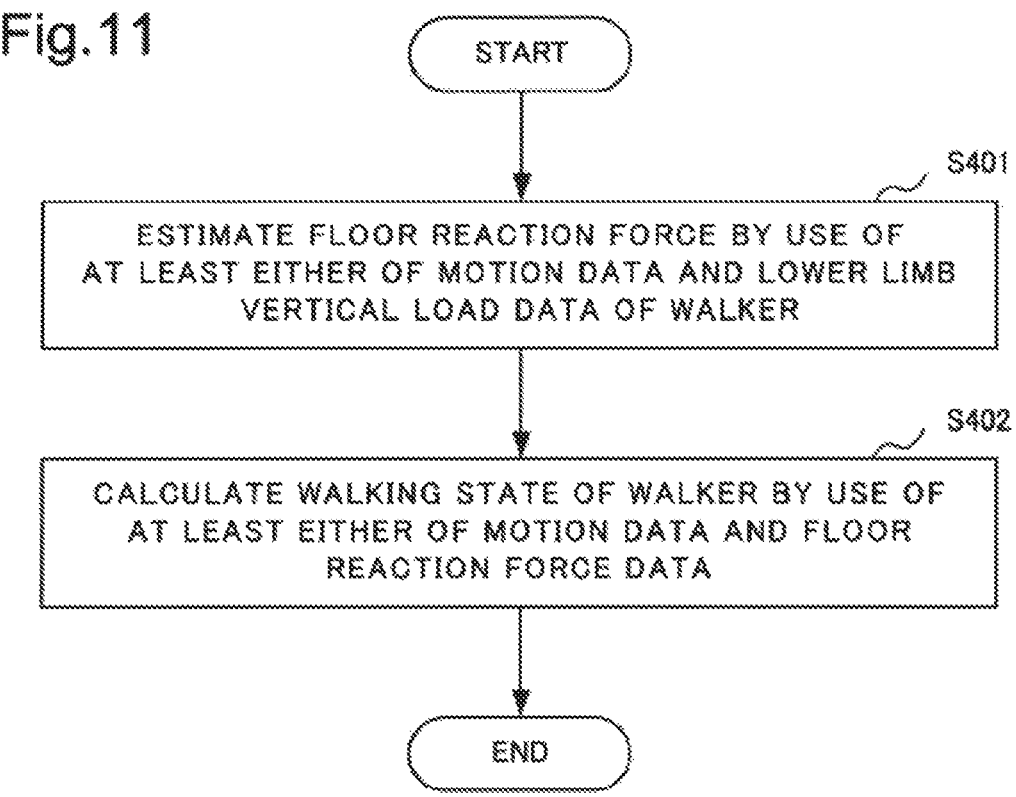
FIG. 11 is a flowchart illustrating an operation example of the walking state measurement device according to the fourth example embodiment of the present invention.

As indicated in FIG. 11, first, the floor reaction force estimation unit 3100 estimates a floor reaction force by use of at least either of motion data and lower limb vertical load data of a walker (Step S401). Next, the walking state calculation unit 3200 calculates a walking state of the walker by use of at least either of the motion data and the floor reaction force data (Step S403).
Description of Effect of Fourth Example Embodiment As described above, the walking state measurement device 3000 according to the fourth example embodiment can provide an effect that adjustment of an arrangement position of a sensor reacting to a floor reaction force, such as a pressure sensor, arranged on a surface of a shoe which a walker wears and walks with becomes unnecessary. The reason is that the walking state measurement device 3000 in the walking state measurement system 1 according to the first example embodiment includes the floor reaction force estimation unit 3100 having a function of estimating a floor reaction force, based on two types of measurement data being motion data and lower limb vertical load data of the walker. For example, a lower limb vertical load may be measured without adjusting an arrangement position of a sensor and also independently of a size and a shape of a foot of the walker, by using the technology described in PTL 2 or the like.

OTHER EXAMPLE EMBODIMENTS

Each of the walking state measurement device according to the first example embodiment, the lower limb motion measurement device according to the second example embodiment, and the walking state measurement device according to the third example embodiment of the present invention may be provided by a computer operating by program control. Each of the walking state measurement device according to the first example embodiment, the lower limb motion measurement device according to the second example embodiment, and the walking state measurement device according to the third example embodiment of the present invention may also be provided by dedicated hardware such as a circuit. Each of the walking state measurement device according to the first example embodiment, the lower limb motion measurement device according to the second example embodiment, and the walking state measurement device according to the third example embodiment of the present invention may also be provided by a combination of the aforementioned computer and dedicated hardware. The aforementioned computer may be a plurality of communicably connected computers. The aforementioned dedicated hardware may be a plurality of communicably connected pieces of dedicated hardware.

Figure 12:
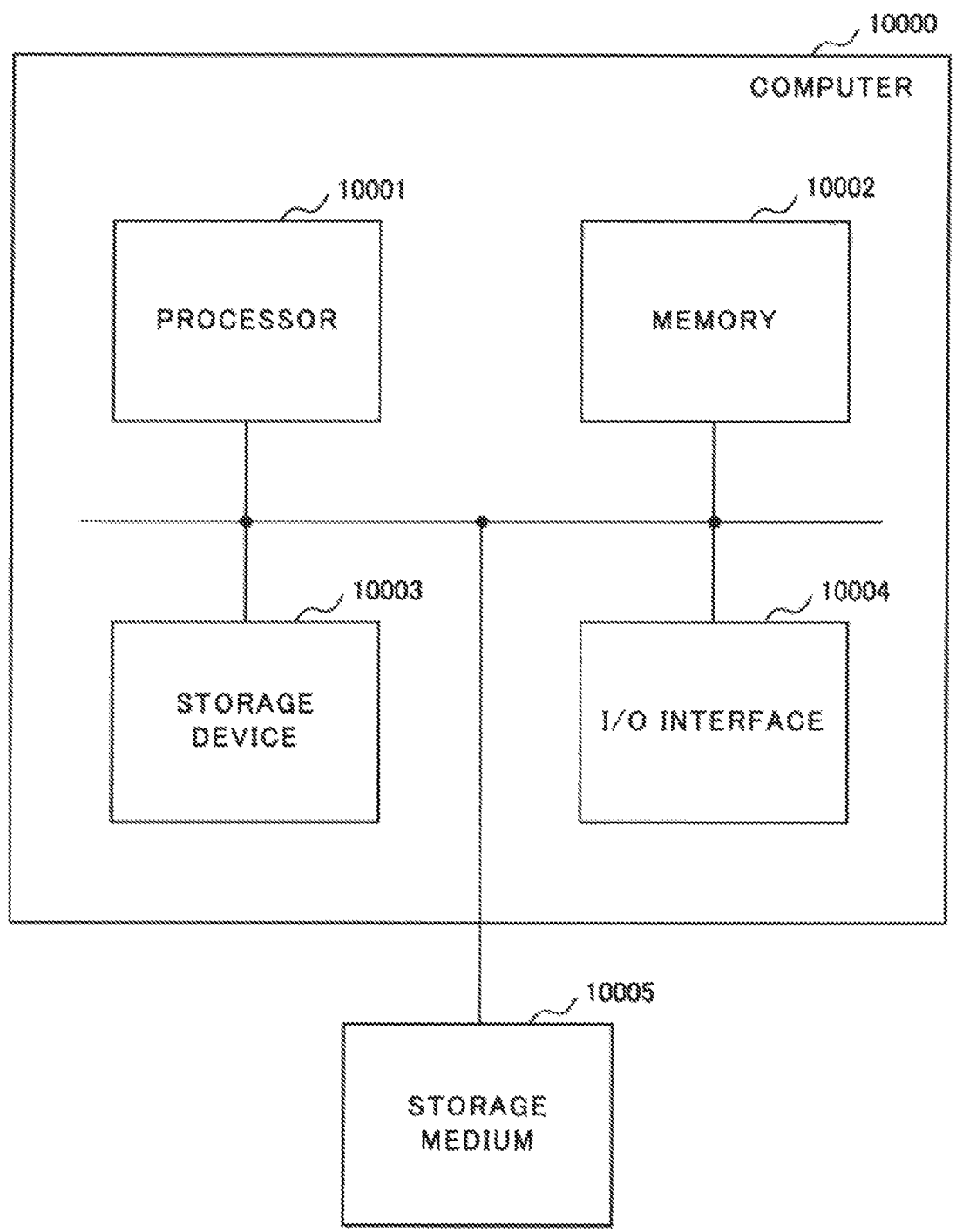
FIG. 12 is a block diagram illustrating a hardware configuration of a computer capable of providing the walking state measurement device, the lower limb motion measurement device, and the walking state measurement device, according to the example embodiments of the present invention.

FIG. 12 is a diagram illustrating a hardware configuration example of a computer 10000 capable of providing the devices according to the example embodiments of the present invention. Referring to FIG. 12, the computer 10000 includes a processor 10001, a memory 10002, a storage device 10003, and an input/output (I/O) interface 10004. Further, the computer 10000 can access a storage medium 10005. For example, each of the memory 10002 and the storage device 10003 is a storage device such as a random access memory (RAM) or a hard disk. For example, the storage medium 10005 is a storage device such as a RAM or a hard disk, a read only memory (ROM), or a portable storage medium. The storage device 10003 may be the storage medium 10005. The processor 10001 can read and write data and a program from and into the memory 10002 and the storage device 10003. For example, the processor 10001 can access a display device 5000 and the like through the I/O interface 10004. The processor 10001 can access the storage medium 10005. For example, the aforementioned storage device 4000 may be provided by the storage device 10003, the memory 10002, or a combination of the storage device 10003 and the memory 10002.

For example, the storage medium 10005 stores a program causing the computer 10000 to operate as the lower limb motion measurement device 1100. The processor 10001 loads the program causing the computer 10000 to operate as the lower limb motion measurement device 1100 into the memory 10002, the program being stored in the storage medium 10005. Then, by the program loaded in the memory 10002 being executed by the processor 10001, the computer 10000 operates as the lower limb motion measurement device 1100.

For example, the storage medium 10005 stores a program causing the computer 10000 to operate as the walking state measurement device 3000. The processor 10001 loads the program causing the computer 10000 to operate as the walking state measurement device 3000 into the memory 10002, the program being stored in the storage medium 10005. Then, by the program loaded in the memory 10002 being executed by the processor 10001, the computer 10000 operates as the walking state measurement device 3000.

For example, the motion analysis unit 1170, the floor reaction force estimation unit 3100, the floor reaction force estimation unit 3110, and the walking state calculation unit 3200 may be provided by a dedicated program capable of providing the function of each unit, the program being read into the memory 10002 from the storage medium 10005 storing a program, and the processor 10001 executing the program. The floor reaction force model storage unit 4100, the body data storage unit 4200, and the measurement data storage unit 4300 may be provided by the memory 10002 or the storage device 10003, such as a hard disk device, included in the computer 10000. The motion analysis unit 1170, the floor reaction force estimation unit 3100, the floor reaction force estimation unit 3110, and the walking state calculation unit 3200 may be provided in part or in whole by a dedicated circuit providing the function of each unit. The floor reaction force model storage unit 4100, the body data storage unit 4200, and the measurement data storage unit 4300 may also be provided in part or in whole by a dedicated circuit providing the function of each unit.

Example 1

This example 1 indicates a specific example using the aforementioned walking state measurement system 2 according to the second example embodiment and the aforementioned walking state measurement device 3000 according to second example embodiment.

In an experiment in this example 1, a small-sized wireless multifunctional sensor "TSND121" from ATR-Promotions, Inc. was used for each of the six IMU sensors being the left thigh IMU 1110, the left lower leg IMU 1120, the left foot region IMU 1130, the right thigh IMU 1140, the right lower leg IMU 1150, and the right foot region IMU 1160 in the lower limb motion measurement device 1100. Each of the IMUs for the thigh regions being the left thigh IMU 1110, and the right thigh IMU 1140 was attached with an elastic band in a position between the hip joint and the knee joint, and at the same time in an outside position of the thigh region. Each of the IMUs for the lower leg regions being the left lower leg IMU 1120 and the right lower leg IMU 1150 was attached with an elastic band in a position between the knee joint and the ankle joint, and at the same time in an outside position of the lower leg region. Each of the IMUs for the foot regions being the left foot region IMU 1130 and the right foot region IMU 1160 was attached with an elastic band in a middle position of the third metatarsal body and at the same time in a position on the instep side.

A walking analyzer "STEP AID" (a shoe type load measurement device) from IMAC Co., Ltd. was used as the lower limb vertical load measurement device 2000 for measuring each lower limb vertical load on the left and right sides.

Furthermore, a linear regression model described in the second example embodiment was used as a floor reaction force model. Parameters of the linear regression model were determined in accordance with a least squares method using, as true values, measurement data of a true floor reaction force and motion data measured by use of a force plate and optical motion capture. A musculoskeletal model simulator "OpenSIM" was used as a walking state measurement means.

A walking state in a condition that a walker walks a straight distance of approximately 10 m was measured by use of a walking state measurement system with a specific configuration as described above. Ankle joint torque of the walker was measured as the walking state.

Figure 8A:
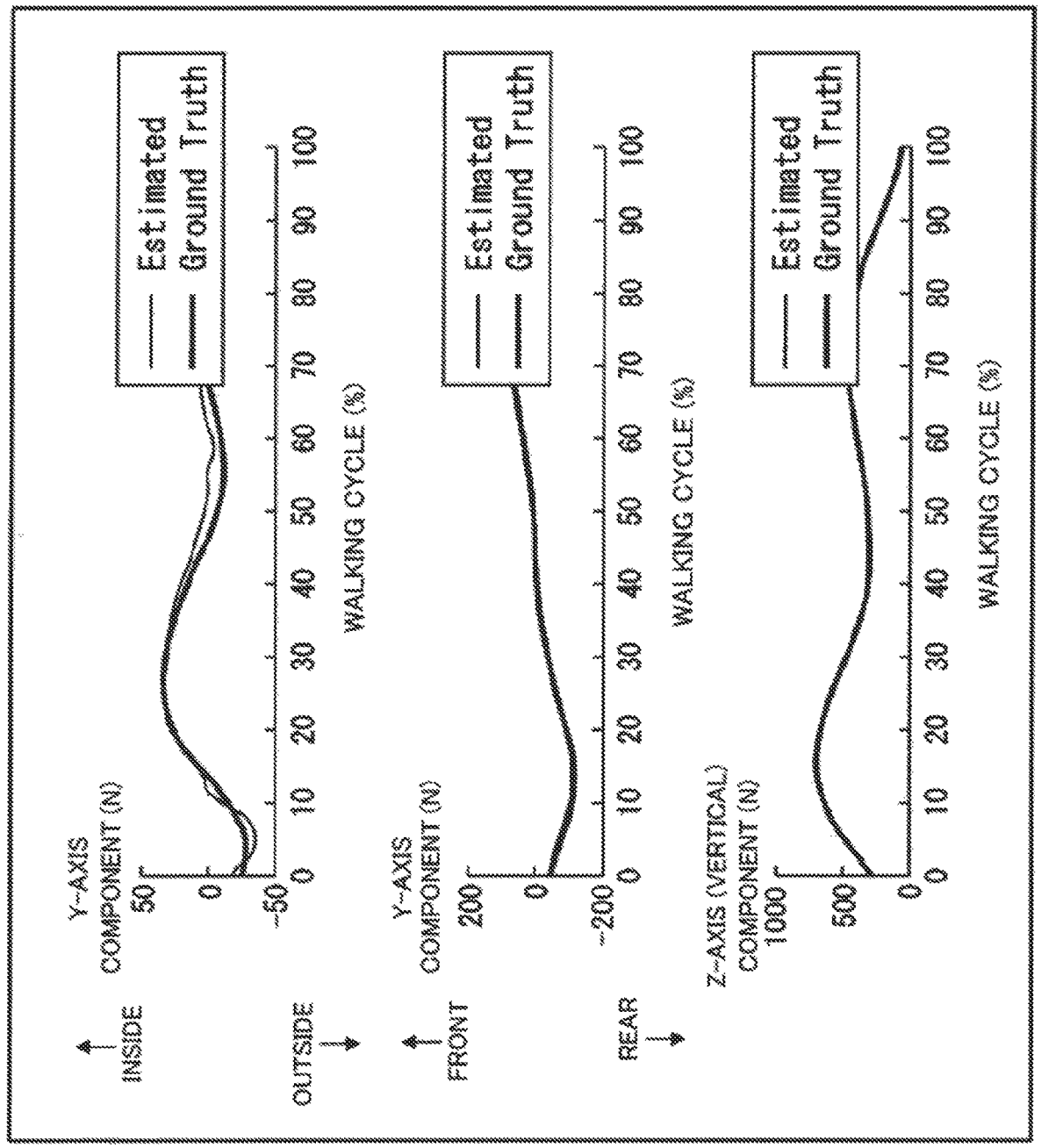
FIG. 8A is a graph illustrating an example of an output result of a floor reaction force estimation unit in an example 1 of the present invention.

Next, an example of a measurement result of a walking state actually measured in this example 1 will be described. FIGS. 8A and 8B are graphs illustrating examples of output results of the floor reaction force estimation unit 3100 in this example 1. FIG. 8A illustrates estimated values (Estimated) and actual measurements (Ground Truth) of three component forces (an X-axis component [lateral component force], a Y-axis component [longitudinal component force], and a Z-axis component [vertical component force]) of floor reaction force data, and FIG. 8B illustrates estimated values (Estimated) and actual measurements (Ground Truth) of coordinates of a point of application of floor reaction force. As illustrated in FIGS. 8A and 8B, it is observed that values extremely close to actual measurements (Ground Truth) are acquired as estimated values (Estimated) of floor reaction force data in the floor reaction force estimation unit 3100 in the walking state measurement device 3000 according to the second example embodiment of the present invention.

Figure 9:
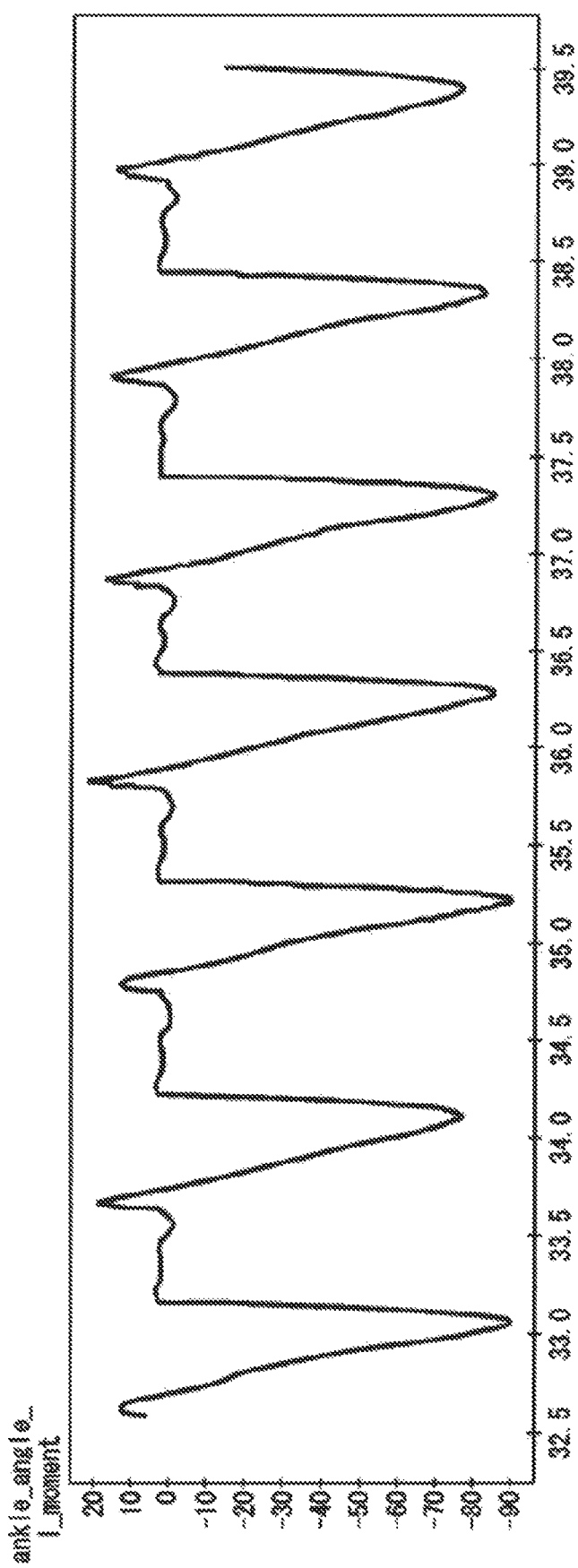
FIG. 9 is a graph illustrating an example of an output result of a walking state calculation unit in the example 1 of the present invention.

FIG. 9 is a graph illustrating an example of an output result of the walking state calculation unit 3200 in this example 1. The graph in FIG. 9 illustrates a case of displaying calculated ankle joint torque (ankle_angle_1_moment) acquired by inputting the actual measurements (Ground Truth) of the floor reaction force data illustrated in FIGS. 8A and 8B into the walking state calculation unit 3200, as an example of a measurement result of a walking state.

From the experimental results in this example 1 as described above, it is proven that the walking state measurement system according to the present invention can accurately measure a walking state of a walker 6000. Accordingly, it is confirmed that an effect that adjustment of an arrangement position of a sensor reacting to a floor reaction force, such as a pressure sensor, arranged on a surface of a shoe which the walker 6000 wears and walks with becomes unnecessary is provided.

The aforementioned example embodiments may also be described in part or in whole as the following Supplementary Notes but are not limited thereto.

Supplementary Note 1

A walking state measurement device including:

a floor reaction force estimation means for estimating a floor reaction force by use of at least either of motion data and lower limb vertical load data of a walker, and outputting the floor reaction force as floor reaction force data; and a walking state calculation means for calculating a walking state of the walker by use of at least either of the motion data and the floor reaction force data, and outputting the walking state.

Supplementary Note 2

The walking state measurement device according to Supplementary Note 1, wherein the walking state calculation means outputs a result of calculating at least either of joint torque and muscle tension, based on inverse dynamic calculation, as the walking state of the walker.

Supplementary Note 3

The walking state measurement device according to Supplementary Note 1 or 2, wherein the floor reaction force estimation means uses, as the motion data, attitude information about each segment when a body of the walker is considered as a rigid body link model.

Supplementary Note 4

The walking state measurement device according to Supplementary Note 3, wherein the floor reaction force estimation means uses, as the motion data, attitude information about at least one of a thigh region and a lower leg region of the walker in attitude information about the each segment when a body of the walker is considered as a rigid body link model.

Supplementary Note 5

The walking state measurement device according to Supplementary Note 1 or 2, wherein the floor reaction force estimation means uses, as the motion data, at least either of acceleration and angular velocity of each segment when a body of the walker is considered as a rigid body link model.

Supplementary Note 6

The walking state measurement device according to any one of Supplementary Notes 1 to 5, wherein the floor reaction force estimation means uses, as the lower limb vertical load data, a result of measuring a lower limb vertical load in each area acquired by dividing a sole surface into two areas.

Supplementary Note 7

A walking state measurement system including:

a motion measurement means for acquiring motion data of a walker;

a lower limb vertical load measurement means for acquiring lower limb vertical load data of the walker; and a walking state measurement means for calculating a walking state of the walker by use of at least either of the motion data acquired in the motion measurement means and the lower limb vertical load data acquired in the lower limb vertical load measurement means, and outputting the walking state.

Supplementary Note 8

The walking state measurement system according to Supplementary Note 7, wherein the walking state measurement means includes:

a floor reaction force estimation means for estimating a floor reaction force by use of at least either of the motion data of the walker acquired by the motion measurement means and the lower limb vertical load data of the walker acquired by the lower limb vertical load measurement means, and outputting the floor reaction force as floor reaction force data; and a walking state calculation means for calculating the walking state of the walker by use of at least either of the motion data and the floor reaction force data, and outputting the walking state.

Supplementary Note 9

The walking state measurement system according to Supplementary Note 8, wherein the walking state calculation means outputs a result of calculating at least either of joint torque and muscle tension, based on inverse dynamic calculation, as the walking state of the walker.

Supplementary Note 10

The walking state measurement system according to Supplementary Note 8 or 9, wherein the floor reaction force estimation means uses, as the motion data, attitude information about each segment when a body of the walker is considered as a rigid body link model.

Supplementary Note 11

The walking state measurement system according to Supplementary Note 10, wherein the floor reaction force estimation means uses, as the motion data, attitude information about at least one of a thigh region and a lower leg region of the walker in attitude information about the each segment when a body of the walker is considered as a rigid body link model.

Supplementary Note 12

The walking state measurement system according to Supplementary Note 8 or 9, wherein the floor reaction force estimation means uses, as the motion data, at least either of acceleration and angular velocity of each segment when a body of the walker is considered as a rigid body link model.

Supplementary Note 13

The walking state measurement system according to any one of Supplementary Notes 8 to 12, wherein the floor reaction force estimation means uses, as the lower limb vertical load data, a result of measuring a lower limb vertical load in each area acquired by dividing a sole surface into two areas.

Supplementary Note 14

A walking state measurement method including:

estimating a floor reaction force by use of at least either of motion data and lower limb vertical load data of a walker, and outputting the floor reaction force as floor reaction force data; and calculating a walking state of the walker by use of at least either of the motion data and the floor reaction force data, and outputting the walking state.

Supplementary Note 15

The walking state measurement method according to Supplementary Note 14, further including outputting a result of calculating at least either of joint torque and muscle tension, based on inverse dynamic calculation, as the walking state of the walker.

Supplementary Note 16

The walking state measurement method according to Supplementary Note 14 or 15, further including using, as the motion data, attitude information about each segment when a body of the walker is considered as a rigid body link model.

Supplementary Note 17

The walking state measurement method according to Supplementary Note 16, further including using, as the motion data, attitude information about at least one of a thigh region and a lower leg region of the walker in attitude information about the each segment when a body of the walker is considered as a rigid body link model.

Supplementary Note 18

The walking state measurement method according to Supplementary Note 14 or 15, further including using, as the motion data, at least either of acceleration and angular velocity of each segment when a body of the walker is considered as a rigid body link model.

Supplementary Note 19

The walking state measurement method according to any one of Supplementary Notes 14 to 18, further including using, as the lower limb vertical load data, a result of measuring a lower limb vertical load in each area acquired by dividing a sole surface into two areas.

Supplementary Note 20

A storage medium for storing a walking state measurement program, the walking state measurement program causing a computer to execute:

walking state measurement processing including:

floor reaction force estimation processing of estimating a floor reaction force by use of at least either of motion data and lower limb vertical load data of a walker, and outputting the floor reaction force as floor reaction force data; and walking state calculation processing of calculating a walking state of the walker by use of at least either of the motion data and the floor reaction force data, and outputting the walking state.

Supplementary Note 21

The storage medium according to Supplementary Note 20, wherein the walking state calculation processing outputs a result of calculating at least either of joint torque and muscle tension, based on inverse dynamic calculation, as the walking state of the walker.

Supplementary Note 22

The storage medium according to Supplementary Note 20 or 21, wherein the floor reaction force estimation processing uses, as the motion data, attitude information about each segment when a body of the walker is considered as a rigid body link model.

Supplementary Note 23

The storage medium according to Supplementary Note 22, wherein the floor reaction force estimation processing uses, as the motion data, attitude information about at least one of a thigh region and a lower leg region of the walker in attitude information about the each segment when a body of the walker is considered as a rigid body link model.

Supplementary Note 24

The storage medium according to Supplementary Note 20 or 21, wherein the floor reaction force estimation processing uses, as the motion data, at least either of acceleration and angular velocity of each segment when a body of the walker is considered as a rigid body link model.

Supplementary Note 25

The storage medium according to any one of Supplementary Notes 20 to 24, wherein the floor reaction force estimation processing uses, as the lower limb vertical load data, a result of measuring a lower limb vertical load in each area acquired by dividing a sole surface into two areas.

Configurations of preferred example embodiments of the present invention have been described above. However, it should be noted that such example embodiments are merely exemplifications of the present invention and do not limit the present invention in any way. A person skilled in the art may easily understand that various modifications and changes may be made to the present invention, based on specific application purposes, without departing from the spirit of the present invention.

This application claims priority based on Japanese Patent Application No. 2016-231395 filed on Nov. 29, 2016, the disclosure of which is hereby incorporated by reference thereto in its entirety.

INDUSTRIAL APPLICABILITY

For example, fields described below may be considered as utilization examples of the present invention.
(1) Real-time diagnosis of walking in daily life
(2) An online diagnosis system presenting a risk of a fall from a walking state (3) A service providing a doctor and a physiotherapist with a walking state of a patient after discharge from the hospital and providing continued care

REFERENCE SIGNS LIST

1 Walking state measurement system
2 Walking state measurement system
3 Walking state measurement system
1000 Motion measurement device
1100 Lower limb motion measurement device
1110 Left thigh IMU
1120 Left lower leg IMU
1130 Left foot region IMU
1140 Right thigh IMU
1150 Right lower leg IMU
1160 Right foot region IMU
1170 Motion analysis unit
2000 Lower limb vertical load measurement device
2100 Lower limb vertical load measurement device
2110 First sensor
2120 Second sensor
3000 Walking state measurement device
3100 Floor reaction force estimation unit
3110 Floor reaction force estimation unit
3200 Walking state calculation unit
4000 Storage device
4100 Floor reaction force model storage unit
4200 Body data storage unit
4300 Measurement data storage unit
5000 Display device
6000 Walker
10000 Computer
10001 Processor
10002 Memory
10003 Storage device
10004 I/O interface
10005 Storage medium

What is claimed is:

1. A walking state measurement device comprising:
at least one memory storing a set of instructions; and
at least one processor configured to execute the set of instructions to:
calculate a ratio between a first lower limb vertical load of a walker and a second lower limb vertical load of the walker, the first lower limb vertical load measured in a first of two areas into which a sole surface of the walker is divided, the second lower limb vertical load measured in a second of the two areas;
estimate a floor reaction force based on the ratio and at least either of motion data and lower limb vertical load data of the walker, and outputting the floor reaction force as floor reaction force data; and
calculate a walking state of the walker based on at least either of the motion data and the floor reaction force data, and outputting the walking state.

2. The walking state measurement device according to claim 1, wherein
the at least one processor is configured to
output a result of calculating at least either of joint torque and muscle tension, based on inverse dynamic calculation, as the walking state of the walker.

3. The walking state measurement device according to claim 1, wherein
the at least one processor is configured to
use, as the motion data, attitude information about each of a plurality of links when a body of the walker is considered as a rigid body link model.

4. The walking state measurement device according to claim 3, wherein
the at least one processor is configured to
use, as the motion data, attitude information about at least one of a thigh region and a lower leg region of the walker in attitude information about each segment link when the body of the walker is considered as the rigid body link model.

5. The walking state measurement device according to claim 1, wherein
the at least one processor is configured to
use, as the motion data, at least either of acceleration and angular velocity of each of a plurality of links when a body of the walker is considered as a rigid body link model.

6. The walking state measurement device according to claim 1, wherein
the at least one processor is configured to
use, as the lower limb vertical load data, a result of measuring the first lower limb vertical load and the second lower limb vertical load.

7. A walking state measurement system including the walking state measurement device according to claim 1, the system comprising:
a motion sensor that acquires the motion data of the walker; and
a lower limb vertical load sensor that acquires the lower limb vertical load data of the walker.

8. A walking state measurement method comprising:
calculating a ratio between a first lower limb vertical load of a walker and a second lower limb vertical load of the walker, the first lower limb vertical load measured in a first of two areas into which a sole surface of the walker is divided, the second lower limb vertical load measured in a second of the two areas;
estimating a floor reaction force based on the ratio and at least either of motion data and lower limb vertical load data of the walker, and outputting the floor reaction force as floor reaction force data; and
calculating a walking state of the walker based on at least either of the motion data and the floor reaction force data, and outputting the walking state.

9. The walking state measurement method according to claim 8, further comprising
outputting a result of calculating at least either of joint torque and muscle tension, based on inverse dynamic calculation, as the walking state of the walker.

10. The walking state measurement method according to claim 8, further comprising
using, as the motion data, attitude information about each of a plurality of links when a body of the walker is considered as a rigid body link model.

11. The walking state measurement method according to claim 10, further comprising
using, as the motion data, attitude information about at least one of a thigh region and a lower leg region of the walker in attitude information about each link when the body of the walker is considered as the rigid body link model.

12. The walking state measurement method according to claim 8, further comprising using, as the motion data, at least either of acceleration and angular velocity of each of a plurality of links when a body of the walker is considered as a rigid body link model.

13. The walking state measurement method according to claim 8, further comprising using, as the lower limb vertical load data, a result of measuring the first lower limb vertical load and the second lower limb vertical load.

14. A non-transitory computer readable storage medium for storing a walking state measurement program causing a computer to execute processing comprising:

calculating a ratio between a first lower limb vertical load of a walker and a second lower limb vertical load of the walker, the first lower limb vertical load measured in a first of two areas into which a sole surface of the walker is divided, the second lower limb vertical load measured in a second of the two areas;

estimating a floor reaction force based on the ratio and at least either of motion data and lower limb vertical load data of the walker, and outputting the floor reaction force as floor reaction force data; and calculating a walking state of the walker based on at least either of the motion data and the floor reaction force data, and outputting the walking state.

15. The storage medium according to claim 14, wherein the processing further comprises:

outputting a result of calculating at least either of joint torque and muscle tension, based on inverse dynamic calculation, as the walking state of the walker.

16. The storage medium according to claim 14, wherein the processing further comprises:

using, as the motion data, attitude information about each of a plurality of links when a body of the walker is considered as a rigid body link model.

17. The storage medium according to claim 16, wherein the processing further comprises:

using, as the motion data, attitude information about at least one of a thigh region and a lower leg region of the walker in attitude information about the each link when the body of the walker is considered as the rigid body link model.

18. The storage medium according to claim 14, wherein the processing further comprises:

using, as the motion data, at least either of acceleration and angular velocity of each link of a plurality of links when a body of the walker is considered as a rigid body link model.

19. The storage medium according to claim 14, wherein the processing further comprises:

using, as the lower limb vertical load data, a result of measuring the first lower limb vertical load and the second lower limb vertical load.

* * * * *